(12) United States Patent
Morris

(10) Patent No.: US 6,229,066 B1
(45) Date of Patent: May 8, 2001

(54) CYTOKININ OXIDASE

(75) Inventor: Roy O. Morris, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/124,541

(22) Filed: Jul. 29, 1998

Related U.S. Application Data

(60) Provisional application No. 60/054,268, filed on Jul. 30, 1997.

(51) Int. Cl.$^7$ ............ C12N 15/82; C12N 5/04; C12N 15/29; A01H 5/00; C07H 21/04

(52) U.S. Cl. ............ 800/279; 536/23.6; 435/69.1; 435/411; 435/320.1; 800/278; 800/295; 800/290; 800/298

(58) Field of Search ............ 536/23.6; 435/69.1, 435/411, 320.1; 800/278, 279, 290, 295, 298

(56) References Cited

U.S. PATENT DOCUMENTS

| | | | |
|---|---|---|---|
| 5,464,758 | 11/1995 | Gossen et al. | 435/69.1 |
| 5,530,196 | 6/1996 | Fraley et al. | 800/298 |
| 5,573,932 | 11/1996 | Ellis et al. | 435/468 |
| 5,750,386 | 5/1998 | Conkling et al. | 800/279 |

OTHER PUBLICATIONS

Whitty, et al., A Cytokinin Oxidase In *Zea Mays,* Can. J. Biochem, vol. 52, pp. 789–799, 1974.
Brownlee, et al., 3–Methyl–2–butenal: An Enzymatic Degradation Product of the Cytokinin, $N^G$–($\Delta^2$–Isopentenyl) adenine, Can. J. Biochem, vol. 53, pp. 37–41, 1975.
Paces et al., Effect of Ribosylzeatin Isomers on the Enzymatic Degradation of $N^6$–($\Delta^2$–isopentenyl) adenosine, Nucleic Acids Research, vol. 3, No. 9, Sep. 1976.
Bradford, M., A Rapid and Sensitive Method for the Quantition of Microgram Quantities of Protein Utilizing the Principle of Protein–Dye Binding, Analytical Biochemistry, vol. 72, pp. 248–254, 1976.
Gupta, et al., Biologically Active Thiazolidinone, J. Indian Chem. Soc., vol. LV, pp. 832–834, 1978.
Bird, et al., The Involvement of Cytokinins in a Host–Parasite Relationship Between the Tomato and Nematode, Parasitology, vol. 80, pp. 497–505, 1980.
McGaw, et al., Cytokinin Catabolism and Cytokinin Oxidase, Phytochemistry, vol. 22, No. 5, pp. 1103–1105, 1983.
McGaw, et al., Cytokinin Oxidase From *Zea mays* Kernels and Vinca Rosea Crown–Gall Tissue, Planta, vol. 159, pp. 30–37, 1983.
Letham, et al., The Biosynthesis and Metabolism of Cytokinins, Ann. Rev. Plant Physiol. vol. 34, pp. 163–197, 1983.

MacDonald, et al., Isolation of Cytokinins by Immunoaffinity Chromatography and Analysis by High–Performance Liquid Chromatography Radioimmunoassay, Methods In Enzymology, vol. 110, pp. 347–358, 1985.
Chatfield, et al., Regulation of Cytokinin Oxidase Activity In Callus Tissues of *Phaseolus Vulgaris* L. cv Great Northern, Plant Physiol., vol. 80, pp. 493–499, 1986.
Chatfield, et al., Cytokinin Oxidase From *Phaseolus Vulgaris* Callus Tissues, Plant Physiol., vol. 84, pp. 726–731, 1987.
Palmer, et al., Substrate Effects on Cytokinin Metabolism In Soybean Callus Tissue, J. Plant Physiol vol. 126, pp. 365–371, 1987.
Chatfield, et al., Cytokinin Oxidase From *Phaseolus Vulgaris* Callus Cultures, Plant Physiol., vol. 88, pp. 245–247, 1988.
Burch, et al., The Purification of Cytokinin Oxidase From *Zea Mays* Kernels, Phytochemistry, vol. 28, No. 5, pp. 1313–1319, 1989.
Laloue, et al., Cytokinin Oxidase From Wheat, Plant Physiol., vol. 90, pp. 899–906, 1989.
Horgan, et al., Cytokinin Oxidase and The Degradative Metabolism of Cytokinins, Abstract of the $13^{th}$ Int'l. Conf. On Plant Growth Substances, pp. 282–290, 1990.
Jones, et al., Hormonal Regulation of Maize Kernel Development The Role of Cytokinins, Proc. Plant Growth Regul. Soc. Am., $17^{th}$, pp. 183–196, 1990.
Kaminek, et al., Genotypic Variation in Cytokinin Oxidase from Phaseolus Callus Cultures, Plant Physiol., vol. 93, pp. 1530–1538, 1990.
Burch, et al., Cytokinin Oxidase and The Degradative Metabolism of Cytokinins, Physiology and Biochemistry of Cytokinins in Plants, pp. 229–232, 1992.
Koziel, et al., Field Performance of Elite Transgenic Maize Plants Expressing an Insecticidal Protein Form *Bacillus Thuringiensis,* Bio/Technology, vol. 11, pp. 194, 1993.
Morris, et al., Cytokinins in Plant Pathogenic Bacteria and Developing Cereal Grains, Aust. J. Plant Physiol., vol. 20, pp. 621–637, 1993.

(List continued on next page.)

*Primary Examiner*—Lynette R. F. Smith
*Assistant Examiner*—Ousama M-Fait Zaphmout
(74) *Attorney, Agent, or Firm*—Senniger, Powers, Leavitt & Roedel

(57) ABSTRACT

An isolated protein which exhibits cytokinin oxidizing activity selected from the group consisting of SEQ. ID No. 1, a protein having an amino acid sequence which includes the amino acid sequence of SEQ. ID No. 1, a protein having an amino acid sequence which includes a portion of the amino acid sequence of SEQ. ID No. 1, the included portion being at least about 20 amino acid residues in length and conferring the cytokinin oxidizing activity on the protein, and a protein including an amino acid sequence with at least about 65% sequence identity to SEQ. ID No. 1, the remainder of amino acid residues being conservatively substituted. Nucleic acids encoding proteins which exhibit cytokinin oxidizing activity and related products and methods are also disclosed.

20 Claims, 8 Drawing Sheets

OTHER PUBLICATIONS

Motyka, et al., Cytokinin Oxidase From Auxin– and Cytokinin–Dependant Callus Cultures of Tobacco, J. Plant Growth Regul., vol. 13, pp. 1–9, 1994.

Hare, et al., Cytokinin Oxidase: Biochemical Features and Physiological Significance, Physiologia Plantarum, vol. 91, pp. 1288–136, 1994.

Meilan, et al., Cloning The Cytokinin Oxidase Gene, Plant Physiol. (Suppl.) 105:68, 1994.

Libreros, et al., A Colorimetric Assay for Cytokinin Oxidase, Analytical Biochemistry, vol. 231, pp. 338–341, 1995.

Wang, J., et al., Cytokinin Oxidase–Purification by Affinity Chromatography and Activation by Caffeic Acid, Plant Science, vol. 112, pp. 161–166, 1995.

Møller, et al., Improved Method for Silver Staining of Glycoproteins in Thin Sodium Dodecyl Sulfate Polyacrylamide Gels, Analytical Biochemistry, vol. 226, pp. 371–374, 1995.

Dietrich, et al., Changes in Cytokinins and Cytokinin Oxidase Activity in Developing Maize Kernels and the Effects of Exogenous Cytokinin on Kernel Development, Plant Physiol. Biochem, vol. 33, No. 3, pp. 327–336, 1995.

Motyka, et al., Changes in Cytokinin Content and Cytokinin Oxidase Activity In Response to Derepression of ipt Gene Transcription in Transgenic Tobacco Calli and Plants, Plant Physiol., vol. 112, pp. 1035–1043, 1996.

Jones, et al., Role and Function of Cytokinin Oxidase in Plants, Plant Growth Regulation, vol. 23, pp. 123–134, 1997.

Kaminek, et al., Regulation of Cytokinin Content in Plant Cells, Physiologia Plantarum, vol. 101, pp. 689–700, 1997.

Wang, et al., Studies of Cytokinin Action and Metabolism Using Tabacco Plants Expressing Either the ipt or the GUS Gene Controlled by a Chalcone Synthase Promoter.II* . ipt and GUS Gene Expression, Cytokinin Levels and Metabolism, Aust. J. Plant Physiol., vol. 24, pp. 673–683, 1997.

Jager, et al., Cytokinin Oxidase Activity in Habituated and Non–habituated Soybean Callus, Plant Growth Regulation vol. 22, pp. 203–206, 1997.

Redig, et al, Physiologia Plantarum, vol. 99, pp. 89–96, 1997.

Shukla, et al., Cytokinin Metabolism and Cytokinin Oxidase And Adenine Phosphoribosyltransferase Activity in Male Sterile Brassica Napus Leaves, Phytochemistry, vol. 44, No. 3, pp. 377–381, 1997.

Kaminek, et al., "Progress in cytokinin research", Trends in Biotechnology, vol. 10, p. 159–164, May 1992, Cambridge, GB.

Burch, L.R., et al., "Cytokinin oxidase and the degradative metabolism of cytokinins", Chemical Abstracts, vol. 119, No. 21, Nov. 22, 1993, abstract No. 221752.

Crespi, M., et al., "R. Fascians (D188) genes for P450 cytochrome, isopentenyltransferase and ferridoxine" EMBL Accession No. z29635, Feb. 15, 1994, XP002086611.

Crespi, M., et al., "Hypothetical 47.9 kD oxidoreductase in fasiation locus (ORF5)" Swissprot Accession No. P46377, Nov. 1, 1995, XP0020866210.

Schreiber B.M.N., et al., "Polyclonal antibodies to maize seedling cytokinin oxidase", Annual Meeting of the American Society of Plant Physiology (Rockville) 108 (2 Suppl.) 1995 80., XP002086604.

Napoli et al. The Plant Cell. 1989. vol. 2: 278–289.*

Tepperman et al. Plant Molecular Biology. 1990. vol. 14: 501–511.*

Boase et al. In Vitro Cell. Deve. Biology. 1998 vol. 34: 46–51.*

* cited by examiner

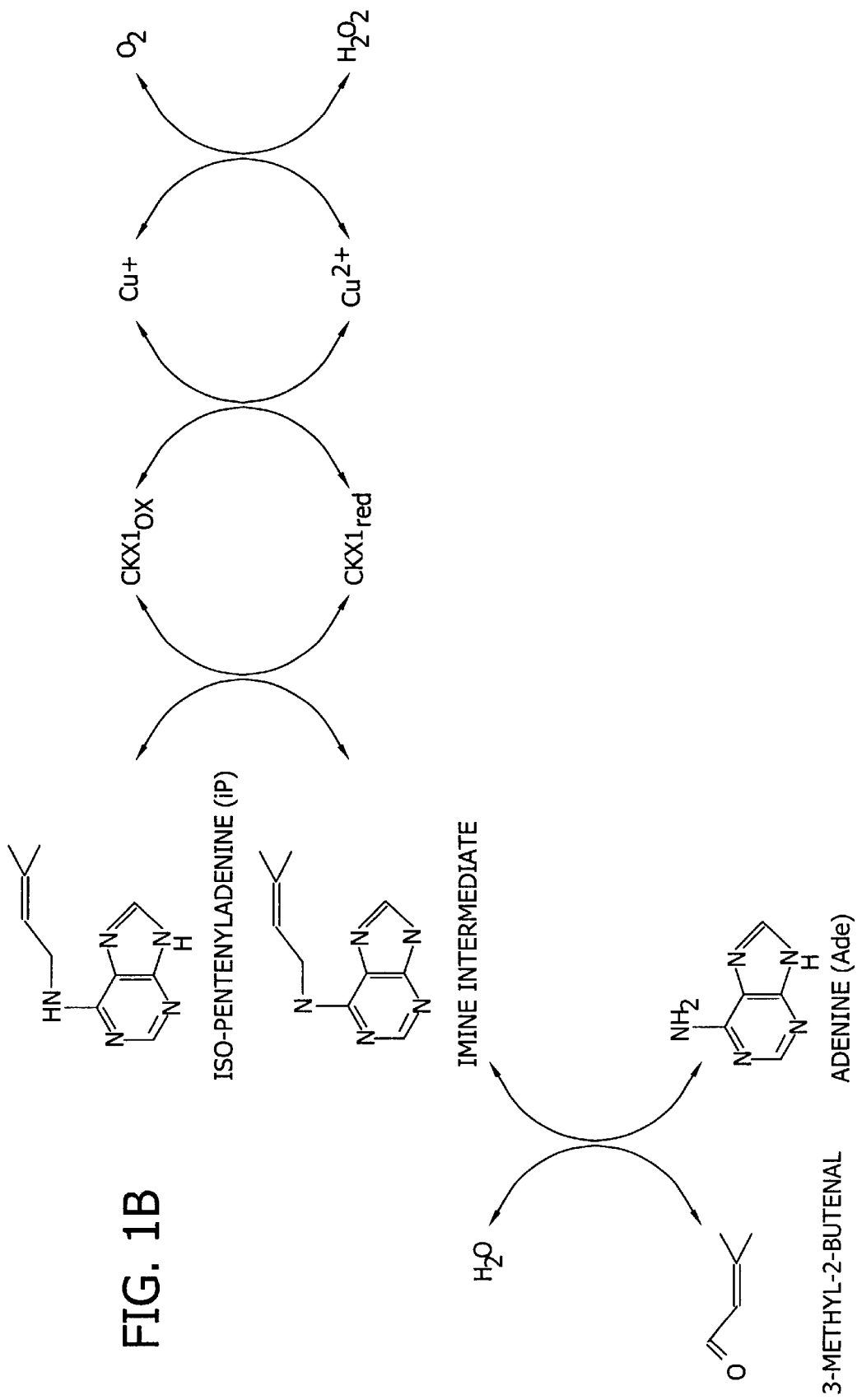

VERIFICATION OF ckx1 GENE INTRON
LOCATIONS BY RT-PCR

VERIFICATION OF ckx1 GENE INTRON
LOCATIONS BY RT-PCR

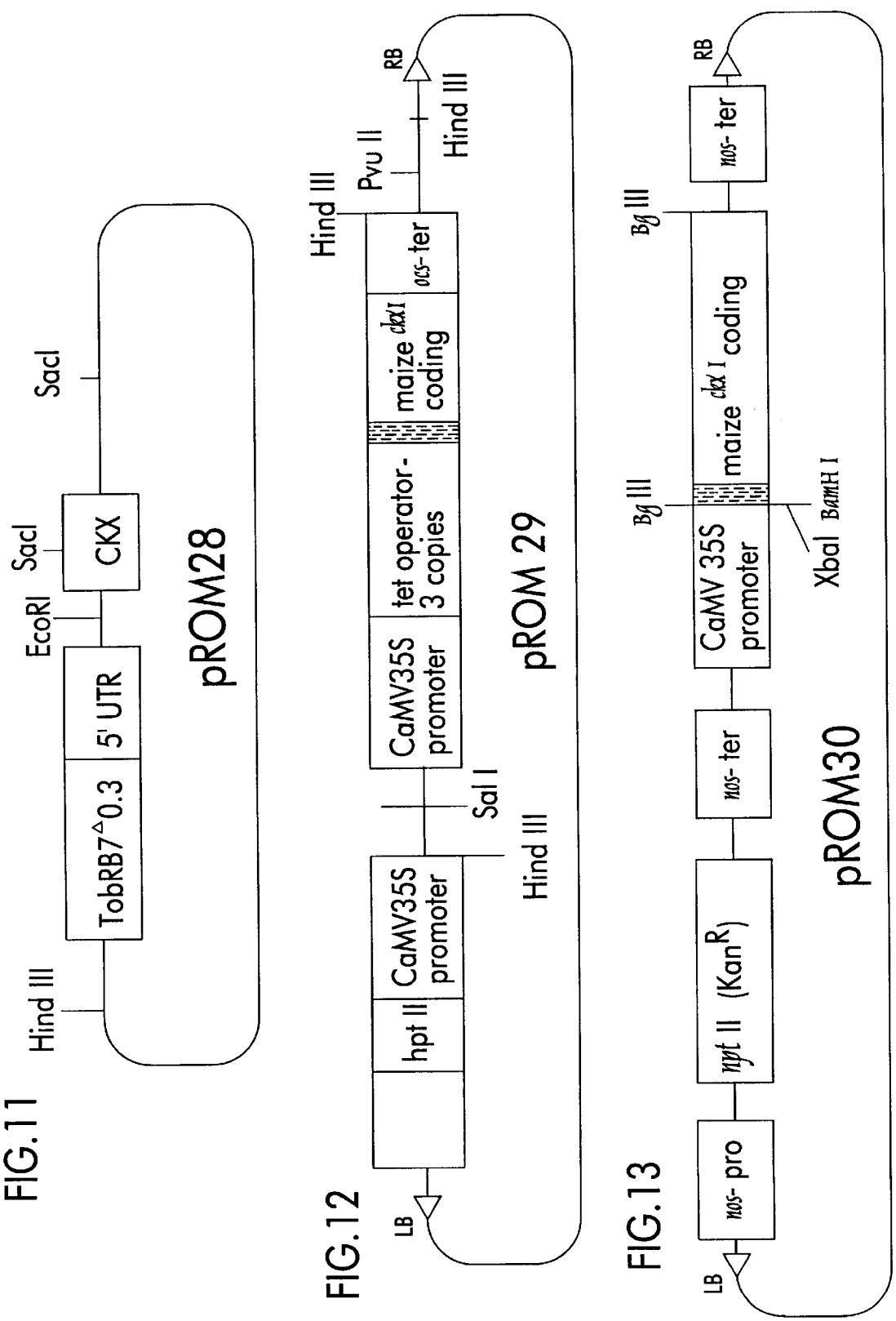
FIG.11 pROM28
FIG.12 pROM 29
FIG.13 pROM30

SEQUENCE LISTING

```
<160> NUMBER OF SEQ ID NOS: 20

<210> SEQ ID NO 1
<211> LENGTH: 534
<212> TYPE: PRT
<213> ORGANISM: Zea mays

<400> SEQUENCE: 1

Met Ala Val Val Tyr Tyr Leu Leu Leu Ala Gly Leu Ile Ala Cys Ser
 1               5                   10                  15

His Ala Leu Ala Ala Gly Thr Pro Ala Leu Gly Asp Asp Arg Gly Arg
            20                  25                  30

Pro Trp Pro Ala Ser Leu Ala Ala Leu Ala Leu Asp Gly Lys Leu Arg
        35                  40                  45

Thr Asp Ser Asn Ala Thr Ala Ala Ser Thr Asp Phe Gly Asn Ile
    50                  55                  60

Thr Ser Ala Leu Pro Ala Ala Val Leu Tyr Pro Ser Ser Thr Gly Asp
 65                  70                  75                  80

Leu Val Ala Leu Leu Ser Ala Ala Asn Ser Thr Pro Gly Trp Pro Tyr
                85                  90                  95

Thr Ile Ala Phe Arg Gly Arg Gly His Ser Leu Met Gly Gln Ala Phe
               100                 105                 110
```

-continued

```
Ala Pro Gly Val Val Asn Met Ala Ser Leu Gly Asp Ala Ala
    115                 120                 125

Ala Pro Pro Gly Ile Asn Val Ser Ala Asp Gly Arg Tyr Val Asp Ala
    130                 135                 140

Gly Gly Glu Gln Val Trp Ile Asp Val Leu Arg Ala Ser Leu Ala Arg
145                 150                 155                 160

Gly Val Ala Pro Arg Ser Trp Asn Asp Tyr Leu Tyr Leu Thr Val Gly
                165                 170                 175

Gly Thr Leu Ser Asn Ala Gly Ile Ser Gly Gln Ala Phe Arg His Gly
            180                 185                 190

Pro Gln Ile Ser Asn Val Leu Glu Met Asp Val Ile Thr Gly His Gly
        195                 200                 205

Glu Met Val Thr Cys Ser Lys Gln Leu Asn Ala Asp Leu Phe Asp Ala
    210                 215                 220

Val Leu Gly Gly Leu Gly Gln Phe Gly Val Ile Thr Arg Ala Arg Ile
225                 230                 235                 240

Ala Val Glu Pro Ala Pro Ala Arg Ala Arg Trp Val Arg Phe Val Tyr
                245                 250                 255

Thr Asp Phe Ala Ala Phe Ser Ala Asp Gln Glu Arg Leu Thr Ala Pro
            260                 265                 270

Arg Pro Gly Gly Gly Ala Ser Phe Gly Pro Met Ser Tyr Val Glu
        275                 280                 285

Gly Ser Val Phe Val Asn Gln Ser Leu Ala Thr Asp Leu Ala Asn Thr
    290                 295                 300

Gly Phe Phe Thr Asp Ala Asp Val Ala Arg Ile Val Ala Leu Ala Gly
305                 310                 315                 320

Glu Arg Asn Ala Thr Thr Val Tyr Ser Ile Glu Ala Thr Leu Asn Tyr
                325                 330                 335

Asp Asn Ala Thr Ala Ala Ala Ala Val Asp Gln Glu Leu Ala Ser
            340                 345                 350

Val Leu Gly Thr Leu Ser Tyr Val Glu Gly Phe Ala Phe Gln Arg Asp
    355                 360                 365

Val Ala Tyr Ala Ala Phe Leu Asp Arg Val His Gly Glu Glu Val Ala
    370                 375                 380

Leu Asn Lys Leu Gly Leu Trp Arg Val Pro His Pro Trp Leu Asn Met
385                 390                 395                 400

Phe Val Pro Arg Ser Arg Ile Ala Asp Phe Asp Arg Gly Val Phe Lys
                405                 410                 415

Gly Ile Leu Gln Gly Thr Asp Ile Val Gly Pro Leu Ile Val Tyr Pro
            420                 425                 430

Leu Asn Lys Ser Met Trp Asp Asp Gly Met Ser Ala Ala Thr Pro Ser
        435                 440                 445

Glu Asp Val Phe Tyr Ala Val Ser Leu Leu Phe Ser Ser Val Ala Pro
    450                 455                 460

Asn Asp Leu Ala Arg Leu Gln Glu Gln Asn Arg Arg Ile Leu Arg Phe
465                 470                 475                 480

Cys Asp Leu Ala Gly Ile Gln Tyr Lys Thr Tyr Leu Ala Arg His Thr
                485                 490                 495

Asp Arg Ser Asp Trp Val Arg His Phe Gly Ala Ala Lys Trp Asn Arg
            500                 505                 510

Phe Val Glu Met Lys Asn Lys Tyr Asp Pro Lys Arg Leu Leu Ser Pro
        515                 520                 525
```

Gly Gln Asp Ile Phe Asn
    530

<210> SEQ ID NO 2
<211> LENGTH: 6733
<212> TYPE: DNA
<213> ORGANISM: Zea mays
<220> FEATURE:
<221> NAME/KEY: gene
<222> LOCATION: (1)..(6733)
<223> OTHER INFORMATION: genomic seqence for a cytokinin oxidase
      from Zea mays
<220> FEATURE:
<221> NAME/KEY: CDS
<222> LOCATION: (1497)..(2111)
<220> FEATURE:
<221> NAME/KEY: CDS
<222> LOCATION: (2524)..(3216)
<220> FEATURE:
<221> NAME/KEY: CDS
<222> LOCATION: (3311)..(3607)
<220> FEATURE:
<221> NAME/KEY: unsure
<222> LOCATION: (5697)

<400> SEQUENCE: 2

| | |
|---|---|
| ctcgagactc cgacgagagg aggctgcgca tgcttgagtc atatcttgga aaaaaaaact | 60 |
| gtaacttaaa gtatgatcta tatatggatt atttggatgg gatgtcattt tcgtatcacc | 120 |
| aaccaaaatt acagtttggt cgtgcgtaga aattctacct actagctgaa caacggctg | 180 |
| ctatgtataa ctactggtac tggaaagaat attagtcatt gactcaaaat tagaatgcat | 240 |
| gtgtaagtca tgcgtgctaa tttgttctat cagcattcgg cgaattccga agtccgtacg | 300 |
| tgttgttcgt ggaggagagg aaaacatcag aaatgacaaa actagacggt gtgtgcttct | 360 |
| acactgaatt cctcaacatt tgttttactt ttactagaga atggcatcaa atggaaaacc | 420 |
| gctgaaaaaa aaacaacaaa acaattggac cccaaatatg tatacagacg ctagctatag | 480 |
| ccagccacac tgaagttgac atgcggcagc tagctagcca ccttctctga aacactaaca | 540 |
| tttgtaccct ggtcgtgtaa gtgtagtagt aacgtatgtt gacgcgactt accgaacaaa | 600 |
| aatataattg tcccaatcaa gctagggacg attgtttgtt tccaaaatgt tgccatttgc | 660 |
| ttaatcaatc ctatattaat tcatggctgt taaggtgaga taaagcgaca agaaatctat | 720 |
| atatatgtat ataagatccc gaaggctagc gacattttg atagcaaaat atgagaagtt | 780 |
| tggcagattg ttctggtagc aaatcaaata atatggccag aataatcgtg gctagcttga | 840 |
| ttaaaccttc atcagcttgg tgtatttgg aagtcgacca accagctggg ggtcgtcgta | 900 |
| cgtagtacca aaattacagc ctgctttcct tcgtcctgta cgtaatgcag tacagctgtc | 960 |
| tagtagagac cattttgagg aggcacacac acattaagtg ataacataaa agacggcctg | 1020 |
| attttatttc ataaccaaac gatatggtca acacacacct atagctacca aatttgtaca | 1080 |
| actatttagt gcgaaaacta tttcattctc aagaattgat cgcttatatt tattattaca | 1140 |
| gcttttaaa tgtataaata cgctatattg catggcaaca gggggtaata attaggcagg | 1200 |
| actatatata taatagtttt ttcttcttct gtaaattctt gggaggatgg taaagttggt | 1260 |
| aactaggcac cttacttgcg cgcatatttt tctgtggtca aacagaataa aactagacgg | 1320 |
| gatgcagaat attttttttcc ttggaaagca gctcatcttt gtgttcgagt aattgaagaa | 1380 |
| gtatgtaatc gcactacacc tacacctata tatacgggg gtgcaatcac ctagttacca | 1440 |
| aacactcaca cataacgtat agctctctct ctctcccgtg aacgacgacg tcgcta atg | 1499 |
| | Met |
| | 1 |

```
gcg gtg gtt tat tac ctg ctg ctg gcc ggg ctg atc gcc tgc tct cat       1547
Ala Val Val Tyr Tyr Leu Leu Leu Ala Gly Leu Ile Ala Cys Ser His
             5                  10                  15 gca cta gcg gca ggc acg cct gcg ctc gga gac gat cgc ggc cgt ccc       1595
Ala Leu Ala Ala Gly Thr Pro Ala Leu Gly Asp Asp Arg Gly Arg Pro
         20                  25                  30 tgg cca gcc tcc ctc gcc gcg ctg gcc ttg gac ggc aag ctc cgg acc       1643
Trp Pro Ala Ser Leu Ala Ala Leu Ala Leu Asp Gly Lys Leu Arg Thr
     35                  40                  45 gac agc aac gcg acg gcg gcg gcc tcg acg gac ttc ggc aac atc acg       1691
Asp Ser Asn Ala Thr Ala Ala Ala Ser Thr Asp Phe Gly Asn Ile Thr
 50                  55                  60                  65 tcg gcg ctc ccg gcg gcg gtc ctg tac ccg tcg tcc acg ggc gac ctg       1739
Ser Ala Leu Pro Ala Ala Val Leu Tyr Pro Ser Ser Thr Gly Asp Leu
                 70                  75                  80 gtg gcg ctg ctg agc gcg gcc aac tcc acc ccg ggg tgg ccc tac acc       1787
Val Ala Leu Leu Ser Ala Ala Asn Ser Thr Pro Gly Trp Pro Tyr Thr
             85                  90                  95 atc gcg ttc cgc ggc cgc ggc cac tcc ctc atg ggc cag gcc ttc gcc       1835
Ile Ala Phe Arg Gly Arg Gly His Ser Leu Met Gly Gln Ala Phe Ala
        100                 105                 110 ccc ggc ggc gtc gtc gtc aac atg gcg tcc ctg ggc gac gcc gcc gcg       1883
Pro Gly Gly Val Val Val Asn Met Ala Ser Leu Gly Asp Ala Ala Ala
    115                 120                 125 ccg ccg cgc atc aac gtg tcc gcg gac ggc cgc tac gtg gac gcc ggc       1931
Pro Pro Arg Ile Asn Val Ser Ala Asp Gly Arg Tyr Val Asp Ala Gly
130                 135                 140                 145 ggc gag cag gtg tgg atc gac gtg ttg cgc gcg tcg ctg gcg cgc ggc       1979
Gly Glu Gln Val Trp Ile Asp Val Leu Arg Ala Ser Leu Ala Arg Gly
                150                 155                 160 gtg gcg ccg cgc tcc tgg aac gac tac ctc tac ctc acc gtc ggc ggc       2027
Val Ala Pro Arg Ser Trp Asn Asp Tyr Leu Tyr Leu Thr Val Gly Gly
            165                 170                 175 acg ctg tcc aac gca ggc atc agc ggc cag gcg ttc cgc cac ggc cca       2075
Thr Leu Ser Asn Ala Gly Ile Ser Gly Gln Ala Phe Arg His Gly Pro
        180                 185                 190 cag ata tct aac gtg ctg gag atg gac gtt atc acc ggtacgtgtg           2121
Gln Ile Ser Asn Val Leu Glu Met Asp Val Ile Thr
    195                 200                 205 cacctactac tacttttttcc ctcccttgca caagtgcaca accacaccac agcaagcgag    2181
caaaagcttg ttttttttt acgtgccagt acacctgcat cgacttctgt tgcttgccac     2241
ggggcaacac cgtgttcaat cagccggatt gaaattcgtt acctacattg cgaatcatat    2301
attatttttt ttagtattat tagtggtgca tggtggttaa tgtccgcgct gcaccggccg    2361 gccgccgcc cggccggcga ggggcggcga cgtctttaat aactagtcat aaatcagcat     2421
gcatgctggc tctcgcagct ggtgcgttga cattgtgcct ttgttcgttt cggctaatag    2481
aattatattg ctggggtgtt gactttgtgg tgatcgaacg ca ggc cat ggg gag       2535
                                              Gly His Gly Glu atg gtg acg tgc tcc aag cag ctg aac gcg gac ctg ttc gac gcc gtc       2583
Met Val Thr Cys Ser Lys Gln Leu Asn Ala Asp Leu Phe Asp Ala Val
210                 215                 220                 225 ctg ggc ggg ctg ggg cag ttc gga gtg atc acc cgg gcc cgg atc gcg       2631
Leu Gly Gly Leu Gly Gln Phe Gly Val Ile Thr Arg Ala Arg Ile Ala
                230                 235                 240 gtg gag ccg gcg ccg gcg cgg gcg cgg tgg gtg cgg ttc gtg tac acc       2679
Val Glu Pro Ala Pro Ala Arg Ala Arg Trp Val Arg Phe Val Tyr Thr
            245                 250                 255
```

-continued

```
gac ttc gcg gcg ttc agc gcc gac cag gag cgg ctg acc gcc ccg cgg    2727
Asp Phe Ala Ala Phe Ser Ala Asp Gln Glu Arg Leu Thr Ala Pro Arg
        260                 265                 270 ccc ggc ggc ggc gcg tcg ttc ggc ccg atg agc tac gtg gaa ggg        2775
Pro Gly Gly Gly Ala Ser Phe Gly Pro Met Ser Tyr Val Glu Gly
    275                 280                 285 tcg gtg ttc gtg aac cag agc ctg gcg acc gac ctg gcg aac acg ggg    2823
Ser Val Phe Val Asn Gln Ser Leu Ala Thr Asp Leu Ala Asn Thr Gly
290                 295                 300                 305 ttc ttc acc gac gcc gac gtc gcc cgg atc gtc gcg ctc gcc ggg gag    2871
Phe Phe Thr Asp Ala Asp Val Ala Arg Ile Val Ala Leu Ala Gly Glu
            310                 315                 320 cgg aac gcc acc acc gtg tac agc atc gag gcc acg ctc aac tac gac    2919
Arg Asn Ala Thr Thr Val Tyr Ser Ile Glu Ala Thr Leu Asn Tyr Asp
                325                 330                 335 aac gcc acg gcg gcg gcg gcg gcg gtg gac cag gag ctc gcg tcc gtg    2967
Asn Ala Thr Ala Ala Ala Ala Ala Val Asp Gln Glu Leu Ala Ser Val
                340                 345                 350 ctg ggc acg ctg agc tac gtg gag ggg ttc gcg ttc cag cgc gac gtg    3015
Leu Gly Thr Leu Ser Tyr Val Glu Gly Phe Ala Phe Gln Arg Asp Val
        355                 360                 365 gcc tac gcg gcg ttc ctt gac cgg gtg cac ggc gag gag gtg gcg ctc    3063
Ala Tyr Ala Ala Phe Leu Asp Arg Val His Gly Glu Glu Val Ala Leu
370                 375                 380                 385 aac aag ctg ggg ctg tgg cgg gtg ccg cac ccg tgg ctc aac atg ttc    3111
Asn Lys Leu Gly Leu Trp Arg Val Pro His Pro Trp Leu Asn Met Phe
            390                 395                 400 gtg ccg cgc tcg cgc atc gcc gac ttc gac cgc ggc gtg ttc aag ggc    3159
Val Pro Arg Ser Arg Ile Ala Asp Phe Asp Arg Gly Val Phe Lys Gly
                405                 410                 415 atc ctg cag ggc acc gac atc gtc ggc ccg ctc atc gtc tac ccc ctc    3207
Ile Leu Gln Gly Thr Asp Ile Val Gly Pro Leu Ile Val Tyr Pro Leu
                420                 425                 430 aac aaa tcc atgtacgtgt tgaatcgatc ggctagctag ctagctaggc            3256
Asn Lys Ser
        435 acgccccggc cggcctctga cgactcgacc ggtctttctg gggtttggtt tttc atg    3313
                                                             Met tgg gac gac ggc atg tcg gcg gcg acg ccg tct gag gac gtg ttc tac    3361
Trp Asp Asp Gly Met Ser Ala Ala Thr Pro Ser Glu Asp Val Phe Tyr
            440                 445                 450 gcg gtg tcg ctg ctc ttc tcg tcg gtg gcg ccc aac gac ctg gcg agg    3409
Ala Val Ser Leu Leu Phe Ser Ser Val Ala Pro Asn Asp Leu Ala Arg
        455                 460                 465 ctg cag gag cag aac agg agg atc ctg cgc ttc tgc gac ctc gcc ggg    3457
Leu Gln Glu Gln Asn Arg Arg Ile Leu Arg Phe Cys Asp Leu Ala Gly
470                 475                 480                 485 atc cag tac aag acc tac ctg gcg cgg cac acg gac cgc agt gac tgg    3505
Ile Gln Tyr Lys Thr Tyr Leu Ala Arg His Thr Asp Arg Ser Asp Trp
            490                 495                 500 gtc cgc cac ttc ggc gcc gcc aag tgg aat cgc ttc gtg gag atg aag    3553
Val Arg His Phe Gly Ala Ala Lys Trp Asn Arg Phe Val Glu Met Lys
        505                 510                 515 aac aag tac gac ccc aag agg ctg ctc tcc ccc ggc cag gac atc ttc    3601
Asn Lys Tyr Asp Pro Lys Arg Leu Leu Ser Pro Gly Gln Asp Ile Phe
        520                 525                 530 aac tga tgatgatagc ccatgcatgt tttagtttct tgggacaata atgtgaataa    3657
Asn
```

-continued

```
ttcccagcta gcggctatta attaatctgt atatagattg atcactgcac tgatgtatgt    3717
caaggtcatt atttacgtta tggtaaaaaa aaaagtaccc tcgtcgtata ttctcgtttc    3777
atctgcccaa cccccagagt tttaaaaatg cacgttgaga gcaaaatttc cacaccgttt    3837
atccatgtag tagattgggt gtatattgaa tccgtataaa tatatagcaa gacaaaattt    3897
attgcaatct gatcccgtac accataattc acatgaaatt agaataaccg aacaaaagga    3957
cttgttagta tgggttgccg ttgcactttt tttgtgtgcc tatttaggta tgatatagtt    4017
ctgccaaaca ttatttgaca gtcaaataca tccctgtcgt cctaataggc gtccaaaatc    4077
aaacgtgtgt ttagccagcc cccatccaaa cacgcccata tccctatttt ctttgccttc    4137
ccttttaatt tttgttttttt tttcctcttc aaataataac tggtcctcaa ctagtcactt    4197
aaaaaaaagg aagagtgtga aggagaagga aaaagacacc gtcacttgtg aaacaaatta    4257
aaaagtttct tggatcgagg cgcgtgatac tctctcaccc tgcacgtttt gcttcgatct    4317
ccgacggcac cgtccgtcat tttctacaaa atacgaaacc ttgttccgtg cttgttgatc    4377
agacagctga cgtcgacaag ttcaggtaaa gggtcatttg cgcgaccagc aggtcggctg    4437
gtgttgaact gattctttta aacttaatga taaccagtag agtagacacc attgattctt    4497
ttaaacttta accgctagtc ttattcaaaa tatttattta aaatgtataa ttttaaatca    4557
agcacagact acatcaagtg ataaaacaaa tcataataaa attaatgata acttattatt    4617
gttttgaata agacgaacga tcaaagtttt aaaaataaac ggtgtcatat acggagggag    4677
tactagctta gtacccccgt tgaccagaag tgcggtgtgc cttaattcga tcgtttctc    4737
ttgtttcctc agcgttcacc acatgcactg cacttgcaag ccgtacacgt tgactagtgg    4797
ggcaatgcta gcttggtgag gtttttttgat tgattcccag cttttagacg aggtcactcc    4857
acaaaaaaag ctaagcaacg gtgctgacct gaataaataa aggtggtcgt agattattgg    4917
ttatagccgt cgtcacaggt cacacacacg caacaagcct atagcaggat tacaccgatt    4977
atcatcggga aatagaaaaa agggaaatga acgaagtaac caggagacag acgacgagaa    5037
agtattgtct atccttaaga ccccccttgag caagctacac ggataattag gctcccatcg    5097
gacgtcattt ctggacacgt acgctattgt gatttgtaag ggtgtttggt ttctaaatac    5157
taatttttag ccactctttta ttattatat ctagtcacta aattatcaaa tacgaaaatt    5217
aaaatagatt tttaatttta agtattttgt aatttatgta ctagaatgga ataaaatggt    5277
gtgattaaaa attagtccct aaaaatcaaa tgtcattccc cctttattag aagacctctt    5337
gagcaagcta agctgcacgt attattaggc ctcaacatgc ctatgtgtgt ataacaggac    5397
aaccaggccc cccaaacttc agttgtacgt atgtgtaaca tgtactgtga ggacaatcga    5457
tctcaaacgt cagctgtagg tacgtatgaa tgtatatatg tgtatttact cctcctgttt    5517
taaatcagtt gtcgcgatgg tatttatgtc catcaaagtt tgttagagta gactagctttt    5577
ttagaaaatg ttagtcacat ttatatcctc aaataaactt acttataaaa ataaattcaa    5637
tgatctattt aataatataa cgatactaat catgtaatat gaatataaat attttcttgn    5697
acatatttga tgaagtttaa aatagttagt ttttaaaaaa ataaaaacac cgactatttt    5757
aaaatagata gagtacatat acaagaaaat gagaaattat tactaatgtt tacaacgtat    5817
aataaataat atataaatta tgaaatatat ttttataata aatctgttta gagaagataa    5877
tatttctac gactccttgt tcaaatctag aatgacatta ttttttgggac ggaggcagtt    5937
cgtactacgt acgtaacatg tattcctaac acggacaatc aaaacatggg aacttcactc    5997
catttgtaaa gccgggggcg gaatcggtgg amgtgtttgt tcttggcgc acggtgaytc    6057
```

```
gatgaggatt cgtgcaaacc ttaamaggct tggtcatctg tctgcattca ytccacacgg      6117
ccatacgcac gtgtttttct ggatgggcat gaacacggac acggcacgca tctcaagtca      6177
gggcagttaa agggagacgc gtgggaacat gataccaggg ttgcatcttc acaaaattgg      6237
ccgtatgtgc tacatcatca gggggagcag ccataattta catggaaacg aatacaatga      6297
tggagcacgt cagtggctat tattcttcaa tgaggctaca gctacactat ttgatgcaca      6357
tcagctactg cctcctagtc cttgggcgcc cacctccaca ctttcagctc gccggagcag      6417
tctccggtga agagcagccc accagccgca agctcgatgg tcctaacttc cttcgtggac      6477
aacagtgttc caatcccgtc gaacctgaaa gatggtaacc aggcaaatgc agagctcctt      6537
tcagtaagga accactgagc gagcggtttg tctatctgat gatgaaactg ataaaaaaaa      6597
attatgcact cacgatggca agtcgagcaa gcggacgcga ttgctgttgt ggagggagca      6657
caagagaact ggcgtcttcc caactcggtg catgccgaag agtgtgcgca aaccctgcaa      6717
cataatcgga aagctt                                                     6733

<210> SEQ ID NO 3
<211> LENGTH: 1605
<212> TYPE: DNA
<213> ORGANISM: Zea mays
<220> FEATURE:
<221> NAME/KEY: CDS
<222> LOCATION: (1)..(1605)

<400> SEQUENCE: 3 atg gcg gtg gtt tat tac ctg ctg ctg gcc ggg ctg atc gcc tgc tct        48
Met Ala Val Val Tyr Tyr Leu Leu Leu Ala Gly Leu Ile Ala Cys Ser
 1               5                  10                  15 cat gca cta gcg gca ggc acg cct gcg ctc gga gac gat cgc ggc cgt        96
His Ala Leu Ala Ala Gly Thr Pro Ala Leu Gly Asp Asp Arg Gly Arg
             20                  25                  30 ccc tgg cca gcc tcc ctc gcc gcg ctg gcc ttg gac ggc aag ctc cgg       144
Pro Trp Pro Ala Ser Leu Ala Ala Leu Ala Leu Asp Gly Lys Leu Arg
         35                  40                  45 acc gac agc aac gcg acg gcg gcg gcc tcg acg gac ttc ggc aac atc       192
Thr Asp Ser Asn Ala Thr Ala Ala Ala Ser Thr Asp Phe Gly Asn Ile
 50                  55                  60 acg tcg gcg ctc ccg gcg gcg gtc ctg tac ccg tcg tcc acg ggc gac       240
Thr Ser Ala Leu Pro Ala Ala Val Leu Tyr Pro Ser Ser Thr Gly Asp
 65                  70                  75                  80 ctg gtg gcg ctg ctg agc gcg gcc aac tcc acc ccg ggg tgg ccc tac       288
Leu Val Ala Leu Leu Ser Ala Ala Asn Ser Thr Pro Gly Trp Pro Tyr
             85                  90                  95 acc atc gcg ttc cgc ggc cgc ggc cac tcc ctc atg ggc cag gcc ttc       336
Thr Ile Ala Phe Arg Gly Arg Gly His Ser Leu Met Gly Gln Ala Phe
            100                 105                 110 gcc ccc ggc ggc gtc gtc gtc aac atg gcg tcc ctg ggc gac gcc gcc       384
Ala Pro Gly Gly Val Val Val Asn Met Ala Ser Leu Gly Asp Ala Ala
        115                 120                 125 gcg ccg ccg cgc atc aac gtg tcc gcg gac ggc cgc tac gtg gac gcc       432
Ala Pro Pro Arg Ile Asn Val Ser Ala Asp Gly Arg Tyr Val Asp Ala
    130                 135                 140 ggc ggc gag cag gtg tgg atc gac gtg ttg cgc gcg tcg ctg gcg cgc       480
Gly Gly Glu Gln Val Trp Ile Asp Val Leu Arg Ala Ser Leu Ala Arg
145                 150                 155                 160 ggc gtg gcg ccg cgc tcc tgg aac gac tac ctc tac ctc acc gtc ggc       528
Gly Val Ala Pro Arg Ser Trp Asn Asp Tyr Leu Tyr Leu Thr Val Gly
                165                 170                 175
```

-continued

```
ggc acg ctg tcc aac gca ggc atc agc ggc cag gcg ttc cgc cac ggc     576
Gly Thr Leu Ser Asn Ala Gly Ile Ser Gly Gln Ala Phe Arg His Gly
            180                 185                 190 cca cag ata tct aac gtg ctg gag atg gac gtt atc acc ggc cat ggg     624
Pro Gln Ile Ser Asn Val Leu Glu Met Asp Val Ile Thr Gly His Gly
        195                 200                 205 gag atg gtg acg tgc tcc aag cag ctg aac gcg gac ctg ttc gac gcc     672
Glu Met Val Thr Cys Ser Lys Gln Leu Asn Ala Asp Leu Phe Asp Ala
    210                 215                 220 gtc ctg ggc ggg ctg ggg cag ttc gga gtg atc acc cgg gcc cgg atc     720
Val Leu Gly Gly Leu Gly Gln Phe Gly Val Ile Thr Arg Ala Arg Ile
225                 230                 235                 240 gcg gtg gag ccg gcg ccg gcg cgg gcg cgg tgg gtg cgg ttc gtg tac     768
Ala Val Glu Pro Ala Pro Ala Arg Ala Arg Trp Val Arg Phe Val Tyr
                245                 250                 255 acc gac ttc gcg gcg ttc agc gcc gac cag gag cgg ctg acc gcc ccg     816
Thr Asp Phe Ala Ala Phe Ser Ala Asp Gln Glu Arg Leu Thr Ala Pro
            260                 265                 270 cgg ccc ggc ggc ggc ggc gcg tcg ttc ggc ccg atg agc tac gtg gaa     864
Arg Pro Gly Gly Gly Gly Ala Ser Phe Gly Pro Met Ser Tyr Val Glu
        275                 280                 285 ggg tcg gtg ttc gtg aac cag agc ctg gcg acc gac ctg gcg aac acg     912
Gly Ser Val Phe Val Asn Gln Ser Leu Ala Thr Asp Leu Ala Asn Thr
    290                 295                 300 ggg ttc ttc acc gac gcc gac gtc gcc cgg atc gtc gcg ctc gcc ggg     960
Gly Phe Phe Thr Asp Ala Asp Val Ala Arg Ile Val Ala Leu Ala Gly
305                 310                 315                 320 gag cgg aac gcc acc acc gtg tac agc atc gag gcc acg ctc aac tac    1008
Glu Arg Asn Ala Thr Thr Val Tyr Ser Ile Glu Ala Thr Leu Asn Tyr
                325                 330                 335 gac aac gcc acg gcg gcg gcg gcg gcg gtg gac cag gag ctc gcg tcc    1056
Asp Asn Ala Thr Ala Ala Ala Ala Val Asp Gln Glu Leu Ala Ser
            340                 345                 350 gtg ctg ggc acg ctg agc tac gtg gag ggg ttc gcg ttc cag cgc gac    1104
Val Leu Gly Thr Leu Ser Tyr Val Glu Gly Phe Ala Phe Gln Arg Asp
        355                 360                 365 gtg gcc tac gcg gcg ttc ctt gac cgg gtg cac ggc gag gag gtg gcg    1152
Val Ala Tyr Ala Ala Phe Leu Asp Arg Val His Gly Glu Glu Val Ala
    370                 375                 380 ctc aac aag ctg ggg ctg tgg cgg gtg ccg cac ccg tgg ctc aac atg    1200
Leu Asn Lys Leu Gly Leu Trp Arg Val Pro His Pro Trp Leu Asn Met
385                 390                 395                 400 ttc gtg ccg cgc tcg cgc atc gcc gac ttc gac cgc ggc gtg ttc aag    1248
Phe Val Pro Arg Ser Arg Ile Ala Asp Phe Asp Arg Gly Val Phe Lys
                405                 410                 415 ggc atc ctg cag ggc acc gac atc gtc ggc ccg ctc atc gtc tac ccc    1296
Gly Ile Leu Gln Gly Thr Asp Ile Val Gly Pro Leu Ile Val Tyr Pro
            420                 425                 430 ctc aac aaa tcc atg tgg gac gac ggc atg tcg gcg gcg acg ccg tct    1344
Leu Asn Lys Ser Met Trp Asp Asp Gly Met Ser Ala Ala Thr Pro Ser
        435                 440                 445 gag gac gtg ttc tac gcg gtg tcg ctc ctc ttc tcg tcg gtg gcg ccc    1392
Glu Asp Val Phe Tyr Ala Val Ser Leu Leu Phe Ser Ser Val Ala Pro
    450                 455                 460 aac gac ctg gcg agg ctg cag gag cag aac agg agg atc ctg cgc ttc    1440
Asn Asp Leu Ala Arg Leu Gln Glu Gln Asn Arg Arg Ile Leu Arg Phe
465                 470                 475                 480 tgc gac ctc gcc ggg atc cag tac aag acc tac ctg gcg cgg cac acg    1488
Cys Asp Leu Ala Gly Ile Gln Tyr Lys Thr Tyr Leu Ala Arg His Thr
```

```
                     485                 490                 495
gac cgc agt gac tgg gtc cgc cac ttc ggc gcc gcc aag tgg aat cgc    1536
Asp Arg Ser Asp Trp Val Arg His Phe Gly Ala Ala Lys Trp Asn Arg
            500                 505                 510 ttc gtg gag atg aag aac aag tac gac ccc aag agg ctg ctc tcc ccc    1584
Phe Val Glu Met Lys Asn Lys Tyr Asp Pro Lys Arg Leu Leu Ser Pro
        515                 520                 525 ggc cag gac atc ttc aac tga                                        1605
Gly Gln Asp Ile Phe Asn
    530

<210> SEQ ID NO 4
<211> LENGTH: 21
<212> TYPE: PRT
<213> ORGANISM: Zea mays
<220> FEATURE:
<221> NAME/KEY: VARIANT
<222> LOCATION: (9)

<400> SEQUENCE: 4

Tyr Val Glu Gly Ser Val Phe Val Xaa Gln Ser Leu Ala Thr Asp Leu
 1               5                  10                  15

Ala Asn Thr Gly Phe
            20

<210> SEQ ID NO 5
<211> LENGTH: 15
<212> TYPE: PRT
<213> ORGANISM: Zea mays

<400> SEQUENCE: 5

Gly Ile Leu Gln Gly Thr Asp Ile Val Gly Pro Leu Ile Val Tyr
 1               5                  10                  15

<210> SEQ ID NO 6
<211> LENGTH: 23
<212> TYPE: DNA
<213> ORGANISM: Zea mays
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i

<400> SEQUENCE: 6
tacgtngayg gnwsngtntt cgt                                          23

<210> SEQ ID NO 7
<211> LENGTH: 23
<212> TYPE: DNA
<213> ORGANISM: Zea mays
<220> FEATURE:
<221> NAME/KEY: modified_base
<222> LOCATION: (3)
<223> OTHER INFORMATION: i
<220> FEATURE:
<221> NAME/KEY: modified_base
```

```
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i

<400> SEQUENCE: 7
acngayctng cnaacacngg ntt                                            23

<210> SEQ ID NO 8
<211> LENGTH: 23
<212> TYPE: DNA
<213> ORGANISM: Zea mays
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i

<400> SEQUENCE: 8
ccntargang tcccntgnct rta                                            23

<210> SEQ ID NO 9
<211> LENGTH: 23
<212> TYPE: DNA
<213> ORGANISM: Zea mays
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (21)
<223> OTHER INFORMATION: i

<400> SEQUENCE: 9
tarcanccng gngantarca nat                                            23

<210> SEQ ID NO 10
<211> LENGTH: 1602
<212> TYPE: DNA
```

```
<213> ORGANISM: Zea mays
<220> FEATURE:
<221> NAME/KEY: variation
<222> LOCATION: (6)
<223> OTHER INFORMATION: a,g,c or t
<220> FEATURE:
<221> NAME/KEY: variation
<222> LOCATION: (9)
<223> OTHER INFORMATION: a,g,c or t
<220> FEATURE:
<221> NAME/KEY: variation
<222> LOCATION: (12)
<223> OTHER INFORMATION: a,g,c or t
<220> FEATURE:
<221> NAME/KEY: variation
<222> LOCATION: (21)
<223> OTHER INFORMATION: a,g,c or t
<220> FEATURE:
<221> NAME/KEY: variation
<222> LOCATION: (24)
<223> OTHER INFORMATION: a,g,c or t
<220> FEATURE:
<221> NAME/KEY: variation
<222> LOCATION: (27)
<223> OTHER INFORMATION: a,g,c or t
<220> FEATURE:
<221> NAME/KEY: variation
<222> LOCATION: (30)
<223> OTHER INFORMATION: a,g,c or t
<220> FEATURE:
<221> NAME/KEY: variation
<222> LOCATION: (33)
<223> OTHER INFORMATION: a,g,c or t
<220> FEATURE:
<221> NAME/KEY: variation
<222> LOCATION: (36)
<223> OTHER INFORMATION: a,g,c or t
<220> FEATURE:
<221> NAME/KEY: variation
<222> LOCATION: (42)
<223> OTHER INFORMATION: a,g,c or t
<220> FEATURE:
<221> NAME/KEY: variation
<222> LOCATION: (48)
<223> OTHER INFORMATION: a,g,c or t
<220> FEATURE:
<221> NAME/KEY: variation
<222> LOCATION: (54)
<223> OTHER INFORMATION: a,g,c or t
<220> FEATURE:
<221> NAME/KEY: variation
<222> LOCATION: (57)
<223> OTHER INFORMATION: a,g,c or t
<220> FEATURE:
<221> NAME/KEY: variation
<222> LOCATION: (60)
<223> OTHER INFORMATION: a,c,g or t
<220> FEATURE:
<221> NAME/KEY: variation
<222> LOCATION: (63)
<223> OTHER INFORMATION: a,g,c or t
<220> FEATURE:
<221> NAME/KEY: variation
<222> LOCATION: (66)
<223> OTHER INFORMATION: a,g,c or t
<220> FEATURE:
<221> NAME/KEY: variation
<222> LOCATION: (69)
<223> OTHER INFORMATION: a,g,c or t
<220> FEATURE:
<221> NAME/KEY: variation
<222> LOCATION: (72)
<223> OTHER INFORMATION: a,g,c or t
<220> FEATURE:
<221> NAME/KEY: variation
<222> LOCATION: (75)
<223> OTHER INFORMATION: a,g,c or t
<220> FEATURE:
<221> NAME/KEY: variation
```

```
<222> LOCATION: (78)
<223> OTHER INFORMATION: a,g,c or t
<220> FEATURE:
<221> NAME/KEY: variation
<222> LOCATION: (81)
<223> OTHER INFORMATION: a,g,c or t
<220> FEATURE:
<221> NAME/KEY: variation
<222> LOCATION: (90)
<223> OTHER INFORMATION: a,g,c or t
<220> FEATURE:
<221> NAME/KEY: variation
<222> LOCATION: (93)
<223> OTHER INFORMATION: a,g,c or t
<220> FEATURE:
<221> NAME/KEY: variation
<222> LOCATION: (96)
<223> OTHER INFORMATION: a,g,c or t
<220> FEATURE:
<221> NAME/KEY: variation
<222> LOCATION: (99)
<223> OTHER INFORMATION: a,g,c or t
<220> FEATURE:
<221> NAME/KEY: variation
<222> LOCATION: (105)
<223> OTHER INFORMATION: a,g,c or t
<220> FEATURE:
<221> NAME/KEY: variation
<222> LOCATION: (108)
<223> OTHER INFORMATION: a,g,c or t
<220> FEATURE:
<221> NAME/KEY: variation
<222> LOCATION: (111)
<223> OTHER INFORMATION: a,g,c or t
<220> FEATURE:
<221> NAME/KEY: variation
<222> LOCATION: (114)
<223> OTHER INFORMATION: a,g,c or t
<220> FEATURE:
<221> NAME/KEY: variation
<222> LOCATION: (117)
<223> OTHER INFORMATION: a,g,c or t
<220> FEATURE:
<221> NAME/KEY: variation
<222> LOCATION: (120)
<223> OTHER INFORMATION: a,g,c or t
<220> FEATURE:
<221> NAME/KEY: variation
<222> LOCATION: (123)
<223> OTHER INFORMATION: a,g,c or t
<220> FEATURE:
<221> NAME/KEY: variation
<222> LOCATION: (126)
<223> OTHER INFORMATION: a,g,c or t
<220> FEATURE:
<221> NAME/KEY: variation
<222> LOCATION: (129)
<223> OTHER INFORMATION: a,g,c or t
<220> FEATURE:
<221> NAME/KEY: variation
<222> LOCATION: (135)
<223> OTHER INFORMATION: a,g,c or t
<220> FEATURE:
<221> NAME/KEY: variation
<222> LOCATION: (141)
<223> OTHER INFORMATION: a,g,c or t
<220> FEATURE:
<221> NAME/KEY: variation
<222> LOCATION: (144)
<223> OTHER INFORMATION: a,g,c or t
<220> FEATURE:
<221> NAME/KEY: variation
<222> LOCATION: (147)
<223> OTHER INFORMATION: a,g,c or t
<220> FEATURE:
<221> NAME/KEY: variation
<222> LOCATION: (153)
<223> OTHER INFORMATION: a,g,c or t
<220> FEATURE:
```

```
<221> NAME/KEY: variation
<222> LOCATION: (159)
<223> OTHER INFORMATION: a,c,g or t
<220> FEATURE:
<221> NAME/KEY: variation
<222> LOCATION: (162)
<223> OTHER INFORMATION: a,g,c or t
<220> FEATURE:
<221> NAME/KEY: variation
<222> LOCATION: (165)
<223> OTHER INFORMATION: a,g,c or t
<220> FEATURE:
<221> NAME/KEY: variation
<222> LOCATION: (168)
<223> OTHER INFORMATION: a,g,c or t
<220> FEATURE:
<221> NAME/KEY: variation
<222> LOCATION: (171)
<223> OTHER INFORMATION: a,g,c or t
<220> FEATURE:
<221> NAME/KEY: variation
<222> LOCATION: (174)
<223> OTHER INFORMATION: a,g,c or t
<220> FEATURE:
<221> NAME/KEY: variation
<222> LOCATION: (177)
<223> OTHER INFORMATION: a,g,c or t
<220> FEATURE:
<221> NAME/KEY: variation
<222> LOCATION: (186)
<223> OTHER INFORMATION: a,g,c or t
<220> FEATURE:
<221> NAME/KEY: variation
<222> LOCATION: (195)
<223> OTHER INFORMATION: a,g,c or t
<220> FEATURE:
<221> NAME/KEY: variation
<222> LOCATION: (198)
<223> OTHER INFORMATION: a,g,c or t
<220> FEATURE:
<221> NAME/KEY: variation
<222> LOCATION: (201)
<223> OTHER INFORMATION: a,g,c or t
<220> FEATURE:
<221> NAME/KEY: variation
<222> LOCATION: (204)
<223> OTHER INFORMATION: a,g,c or t
<220> FEATURE:
<221> NAME/KEY: variation
<222> LOCATION: (207)
<223> OTHER INFORMATION: a,g,c or t
<220> FEATURE:
<221> NAME/KEY: variation
<222> LOCATION: (210)
<223> OTHER INFORMATION: a,g,c or t
<220> FEATURE:
<221> NAME/KEY: variation
<222> LOCATION: (213)
<223> OTHER INFORMATION: a,g,c or t
<220> FEATURE:
<221> NAME/KEY: variation
<222> LOCATION: (216)
<223> OTHER INFORMATION: a,g,c or t
<220> FEATURE:
<221> NAME/KEY: variation
<222> LOCATION: (219)
<223> OTHER INFORMATION: a,g,c or t
<220> FEATURE:
<221> NAME/KEY: variation
<222> LOCATION: (225)
<223> OTHER INFORMATION: a,g,c or t
<220> FEATURE:
<221> NAME/KEY: variation
<222> LOCATION: (228)
<223> OTHER INFORMATION: a,g,c or t
<220> FEATURE:
<221> NAME/KEY: variation
<222> LOCATION: (231)
<223> OTHER INFORMATION: a,g,c or t
```

```
<220> FEATURE:
<221> NAME/KEY: variation
<222> LOCATION: (234)
<223> OTHER INFORMATION: a,g,c or t
<220> FEATURE:
<221> NAME/KEY: variation
<222> LOCATION: (237)
<223> OTHER INFORMATION: a,g,c or t
<220> FEATURE:
<221> NAME/KEY: variation
<222> LOCATION: (243)
<223> OTHER INFORMATION: a,g,c or t
<220> FEATURE:
<221> NAME/KEY: variation
<222> LOCATION: (246)
<223> OTHER INFORMATION: a,g,c or t
<220> FEATURE:
<221> NAME/KEY: variation
<222> LOCATION: (249)
<223> OTHER INFORMATION: a,g,c or t
<220> FEATURE:
<221> NAME/KEY: variation
<222> LOCATION: (252)
<223> OTHER INFORMATION: a,g,c or t
<220> FEATURE:
<221> NAME/KEY: variation
<222> LOCATION: (255)
<223> OTHER INFORMATION: a,c,g or t
<220> FEATURE:
<221> NAME/KEY: variation
<222> LOCATION: (258)
<223> OTHER INFORMATION: a,g,c or t
<220> FEATURE:
<221> NAME/KEY: variation
<222> LOCATION: (261)
<223> OTHER INFORMATION: a,g,c or t
<220> FEATURE:
<221> NAME/KEY: variation
<222> LOCATION: (264)
<223> OTHER INFORMATION: a,g,c or t
<220> FEATURE:
<221> NAME/KEY: variation
<222> LOCATION: (270)
<223> OTHER INFORMATION: a,g,c or t
<220> FEATURE:
<221> NAME/KEY: variation
<222> LOCATION: (273)
<223> OTHER INFORMATION: a,g,c or t
<220> FEATURE:
<221> NAME/KEY: variation
<222> LOCATION: (276)
<223> OTHER INFORMATION: a,g,c or t
<220> FEATURE:
<221> NAME/KEY: variation
<222> LOCATION: (279)
<223> OTHER INFORMATION: a,g,c or t
<220> FEATURE:
<221> NAME/KEY: variation
<222> LOCATION: (285)
<223> OTHER INFORMATION: a,g,c or t
<220> FEATURE:
<221> NAME/KEY: variation
<222> LOCATION: (291)
<223> OTHER INFORMATION: a,g,c or t
<220> FEATURE:
<221> NAME/KEY: variation
<222> LOCATION: (297)
<223> OTHER INFORMATION: a,g,c or t
<220> FEATURE:
<221> NAME/KEY: variation
<222> LOCATION: (303)
<223> OTHER INFORMATION: a,g,c or t
<220> FEATURE:
<221> NAME/KEY: variation
<222> LOCATION: (306)
<223> OTHER INFORMATION: a,g,c or t
<220> FEATURE:
<221> NAME/KEY: variation
<222> LOCATION: (309)
```

-continued

```
<223> OTHER INFORMATION: a,g,c or t
<220> FEATURE:
<221> NAME/KEY: variation
<222> LOCATION: (312)
<223> OTHER INFORMATION: a,g,c or t
<220> FEATURE:
<221> NAME/KEY: variation
<222> LOCATION: (318)
<223> OTHER INFORMATION: a,g,c or t
<220> FEATURE:
<221> NAME/KEY: variation
<222> LOCATION: (321)
<223> OTHER INFORMATION: a,g,c or t
<220> FEATURE:
<221> NAME/KEY: variation
<222> LOCATION: (327)
<223> OTHER INFORMATION: a,g,c or t
<220> FEATURE:
<221> NAME/KEY: variation
<222> LOCATION: (333)
<223> OTHER INFORMATION: a,g,c or t
<220> FEATURE:
<221> NAME/KEY: variation
<222> LOCATION: (339)
<223> OTHER INFORMATION: a,g,c or t
<220> FEATURE:
<221> NAME/KEY: variation
<222> LOCATION: (342)
<223> OTHER INFORMATION: a,g,c or t
<220> FEATURE:
<221> NAME/KEY: variation
<222> LOCATION: (345)
<223> OTHER INFORMATION: a,g,c or t
<220> FEATURE:
<221> NAME/KEY: variation
<222> LOCATION: (348)
<223> OTHER INFORMATION: a,g,c or t
<220> FEATURE:
<221> NAME/KEY: variation
<222> LOCATION: (351)
<223> OTHER INFORMATION: a,g,c or t
<220> FEATURE:
<221> NAME/KEY: variation
<222> LOCATION: (354)
<223> OTHER INFORMATION: a,g,c or t
<220> FEATURE:
<221> NAME/KEY: variation
<222> LOCATION: (357)
<223> OTHER INFORMATION: a,g,c or t
<220> FEATURE:
<221> NAME/KEY: variation
<222> LOCATION: (366)
<223> OTHER INFORMATION: a,c,g or t
<220> FEATURE:
<221> NAME/KEY: variation
<222> LOCATION: (369)
<223> OTHER INFORMATION: a,g,c or t
<220> FEATURE:
<221> NAME/KEY: variation
<222> LOCATION: (372)
<223> OTHER INFORMATION: a,g,c or t
<220> FEATURE:
<221> NAME/KEY: variation
<222> LOCATION: (375)
<223> OTHER INFORMATION: a,g,c or t
<220> FEATURE:
<221> NAME/KEY: variation
<222> LOCATION: (381)
<223> OTHER INFORMATION: a,g,c or t
<220> FEATURE:
<221> NAME/KEY: variation
<222> LOCATION: (384)
<223> OTHER INFORMATION: a,g,c or t
<220> FEATURE:
<221> NAME/KEY: variation
<222> LOCATION: (387)
<223> OTHER INFORMATION: a,g,c or t
<220> FEATURE:
<221> NAME/KEY: variation
```

-continued

```
<222> LOCATION: (390)
<223> OTHER INFORMATION: a,g,c or t
<220> FEATURE:
<221> NAME/KEY: variation
<222> LOCATION: (393)
<223> OTHER INFORMATION: a,g,c or t
<220> FEATURE:
<221> NAME/KEY: variation
<222> LOCATION: (396)
<223> OTHER INFORMATION: a,g,c or t
<220> FEATURE:
<221> NAME/KEY: variation
<222> LOCATION: (405)
<223> OTHER INFORMATION: a,g,c or t
<220> FEATURE:
<221> NAME/KEY: variation
<222> LOCATION: (408)
<223> OTHER INFORMATION: a,g,c or t
<220> FEATURE:
<221> NAME/KEY: variation
<222> LOCATION: (411)
<223> OTHER INFORMATION: a,g,c or t
<220> FEATURE:
<221> NAME/KEY: variation
<222> LOCATION: (417)
<223> OTHER INFORMATION: a,g,c or t
<220> FEATURE:
<221> NAME/KEY: variation
<222> LOCATION: (420)
<223> OTHER INFORMATION: a,g,c or t
<220> FEATURE:
<221> NAME/KEY: variation
<222> LOCATION: (426)
<223> OTHER INFORMATION: a,g,c or t
<220> FEATURE:
<221> NAME/KEY: variation
<222> LOCATION: (432)
<223> OTHER INFORMATION: a,g,c or t
<220> FEATURE:
<221> NAME/KEY: variation
<222> LOCATION: (435)
<223> OTHER INFORMATION: a,g,c or t
<220> FEATURE:
<221> NAME/KEY: variation
<222> LOCATION: (438)
<223> OTHER INFORMATION: a,g,c or t
<220> FEATURE:
<221> NAME/KEY: variation
<222> LOCATION: (447)
<223> OTHER INFORMATION: a,g,c or t
<220> FEATURE:
<221> NAME/KEY: variation
<222> LOCATION: (459)
<223> OTHER INFORMATION: a,g,c or t
<220> FEATURE:
<221> NAME/KEY: variation
<222> LOCATION: (462)
<223> OTHER INFORMATION: a,g,c or t
<220> FEATURE:
<221> NAME/KEY: variation
<222> LOCATION: (465)
<223> OTHER INFORMATION: a,g,c or t
<220> FEATURE:
<221> NAME/KEY: variation
<222> LOCATION: (468)
<223> OTHER INFORMATION: a,g,c or t
<220> FEATURE:
<221> NAME/KEY: variation
<222> LOCATION: (471)
<223> OTHER INFORMATION: a,g,c or t
<220> FEATURE:
<221> NAME/KEY: variation
<222> LOCATION: (474)
<223> OTHER INFORMATION: a,g,c or t
<220> FEATURE:
<221> NAME/KEY: variation
<222> LOCATION: (477)
<223> OTHER INFORMATION: a,c,g or t
<220> FEATURE:
```

```
<221> NAME/KEY: variation
<222> LOCATION: (480)
<223> OTHER INFORMATION: a,g,c or t
<220> FEATURE:
<221> NAME/KEY: variation
<222> LOCATION: (483)
<223> OTHER INFORMATION: a,g,c or t
<220> FEATURE:
<221> NAME/KEY: variation
<222> LOCATION: (486)
<223> OTHER INFORMATION: a,g,c or t
<220> FEATURE:
<221> NAME/KEY: variation
<222> LOCATION: (489)
<223> OTHER INFORMATION: a,g,c or t
<220> FEATURE:
<221> NAME/KEY: variation
<222> LOCATION: (492)
<223> OTHER INFORMATION: a,g,c or t
<220> FEATURE:
<221> NAME/KEY: variation
<222> LOCATION: (495)
<223> OTHER INFORMATION: a,g,c or t
<220> FEATURE:
<221> NAME/KEY: variation
<222> LOCATION: (498)
<223> OTHER INFORMATION: a,g,c or t
<220> FEATURE:
<221> NAME/KEY: variation
<222> LOCATION: (513)
<223> OTHER INFORMATION: a,g,c or t
<220> FEATURE:
<221> NAME/KEY: variation
<222> LOCATION: (519)
<223> OTHER INFORMATION: a,g,c or t
<220> FEATURE:
<221> NAME/KEY: variation
<222> LOCATION: (522)
<223> OTHER INFORMATION: a,g,c or t
<220> FEATURE:
<221> NAME/KEY: variation
<222> LOCATION: (525)
<223> OTHER INFORMATION: a,g,c or t
<220> FEATURE:
<221> NAME/KEY: variation
<222> LOCATION: (528)
<223> OTHER INFORMATION: a,g,c or t
<220> FEATURE:
<221> NAME/KEY: variation
<222> LOCATION: (531)
<223> OTHER INFORMATION: a,g,c or t
<220> FEATURE:
<221> NAME/KEY: variation
<222> LOCATION: (534)
<223> OTHER INFORMATION: a,g,c or t
<220> FEATURE:
<221> NAME/KEY: variation
<222> LOCATION: (537)
<223> OTHER INFORMATION: a,g,c or t
<220> FEATURE:
<221> NAME/KEY: variation
<222> LOCATION: (540)
<223> OTHER INFORMATION: a,g,c or t
<220> FEATURE:
<221> NAME/KEY: variation
<222> LOCATION: (546)
<223> OTHER INFORMATION: a,g,c or t
<220> FEATURE:
<221> NAME/KEY: variation
<222> LOCATION: (549)
<223> OTHER INFORMATION: a,g,c or t
<220> FEATURE:
<221> NAME/KEY: variation
<222> LOCATION: (555)
<223> OTHER INFORMATION: a,g,c or t
<220> FEATURE:
<221> NAME/KEY: variation
<222> LOCATION: (558)
<223> OTHER INFORMATION: a,g,c or t
```

-continued

```
<220> FEATURE:
<221> NAME/KEY: variation
<222> LOCATION: (564)
<223> OTHER INFORMATION: a,g,c or t
<220> FEATURE:
<221> NAME/KEY: variation
<222> LOCATION: (570)
<223> OTHER INFORMATION: a,g,c or t
<220> FEATURE:
<221> NAME/KEY: variation
<222> LOCATION: (576)
<223> OTHER INFORMATION: a,g,c or t
<220> FEATURE:
<221> NAME/KEY: variation
<222> LOCATION: (579)
<223> OTHER INFORMATION: a,g,c or t
<220> FEATURE:
<221> NAME/KEY: variation
<222> LOCATION: (588)
<223> OTHER INFORMATION: a,g,c or t
<220> FEATURE:
<221> NAME/KEY: variation
<222> LOCATION: (594)
<223> OTHER INFORMATION: a,c,g or t
<220> FEATURE:
<221> NAME/KEY: variation
<222> LOCATION: (597)
<223> OTHER INFORMATION: a,g,c or t
<220> FEATURE:
<221> NAME/KEY: variation
<222> LOCATION: (609)
<223> OTHER INFORMATION: a,g,c or t
<220> FEATURE:
<221> NAME/KEY: variation
<222> LOCATION: (615)
<223> OTHER INFORMATION: a,g,c or t
<220> FEATURE:
<221> NAME/KEY: variation
<222> LOCATION: (618)
<223> OTHER INFORMATION: a,g,c or t
<220> FEATURE:
<221> NAME/KEY: variation
<222> LOCATION: (624)
<223> OTHER INFORMATION: a,g,c or t
<220> FEATURE:
<221> NAME/KEY: variation
<222> LOCATION: (633)
<223> OTHER INFORMATION: a,g,c or t
<220> FEATURE:
<221> NAME/KEY: variation
<222> LOCATION: (637)
<223> OTHER INFORMATION: a,g,c or t
<220> FEATURE:
<221> NAME/KEY: variation
<222> LOCATION: (642)
<223> OTHER INFORMATION: a,g,c or t
<220> FEATURE:
<221> NAME/KEY: variation
<222> LOCATION: (651)
<223> OTHER INFORMATION: a,g,c or t
<220> FEATURE:
<221> NAME/KEY: variation
<222> LOCATION: (657)
<223> OTHER INFORMATION: a,g,c or t
<220> FEATURE:
<221> NAME/KEY: variation
<222> LOCATION: (663)
<223> OTHER INFORMATION: a,g,c or t
<220> FEATURE:
<221> NAME/KEY: variation
<222> LOCATION: (672)
<223> OTHER INFORMATION: a,g,c or t
<220> FEATURE:
<221> NAME/KEY: variation
<222> LOCATION: (675)
<223> OTHER INFORMATION: a,g,c or t
<220> FEATURE:
<221> NAME/KEY: variation
<222> LOCATION: (678)
```

-continued

```
<223> OTHER INFORMATION: a,g,c or t
<220> FEATURE:
<221> NAME/KEY: variation
<222> LOCATION: (681)
<223> OTHER INFORMATION: a,g,c or t
<220> FEATURE:
<221> NAME/KEY: variation
<222> LOCATION: (684)
<223> OTHER INFORMATION: a,g,c or t
<220> FEATURE:
<221> NAME/KEY: variation
<222> LOCATION: (687)
<223> OTHER INFORMATION: a,g,c or t
<220> FEATURE:
<221> NAME/KEY: variation
<222> LOCATION: (690)
<223> OTHER INFORMATION: a,g,c or t
<220> FEATURE:
<221> NAME/KEY: variation
<222> LOCATION: (699)
<223> OTHER INFORMATION: a,g,c or t
<220> FEATURE:
<221> NAME/KEY: variation
<222> LOCATION: (702)
<223> OTHER INFORMATION: a,g,c or t
<220> FEATURE:
<221> NAME/KEY: variation
<222> LOCATION: (708)
<223> OTHER INFORMATION: a,g,c or t
<220> FEATURE:
<221> NAME/KEY: variation
<222> LOCATION: (711)
<223> OTHER INFORMATION: a,g,c or t
<220> FEATURE:
<221> NAME/KEY: variation
<222> LOCATION: (717)
<223> OTHER INFORMATION: a,g,c or t
<220> FEATURE:
<221> NAME/KEY: variation
<222> LOCATION: (723)
<223> OTHER INFORMATION: a,g,c or t
<220> FEATURE:
<221> NAME/KEY: variation
<222> LOCATION: (726)
<223> OTHER INFORMATION: a,g,c or t
<220> FEATURE:
<221> NAME/KEY: variation
<222> LOCATION: (732)
<223> OTHER INFORMATION: a,c,g or t
<220> FEATURE:
<221> NAME/KEY: variation
<222> LOCATION: (735)
<223> OTHER INFORMATION: a,g,c or t
<220> FEATURE:
<221> NAME/KEY: variation
<222> LOCATION: (738)
<223> OTHER INFORMATION: a,g,c or t
<220> FEATURE:
<221> NAME/KEY: variation
<222> LOCATION: (741)
<223> OTHER INFORMATION: a,g,c or t
<220> FEATURE:
<221> NAME/KEY: variation
<222> LOCATION: (744)
<223> OTHER INFORMATION: a,g,c or t
<220> FEATURE:
<221> NAME/KEY: variation
<222> LOCATION: (747)
<223> OTHER INFORMATION: a,g,c or t
<220> FEATURE:
<221> NAME/KEY: variation
<222> LOCATION: (750)
<223> OTHER INFORMATION: a,g,c or t
<220> FEATURE:
<221> NAME/KEY: variation
<222> LOCATION: (756)
<223> OTHER INFORMATION: a,g,c or t
<220> FEATURE:
<221> NAME/KEY: variation
```

```
<222> LOCATION: (759)
<223> OTHER INFORMATION: a,g,c or t
<220> FEATURE:
<221> NAME/KEY: variation
<222> LOCATION: (765)
<223> OTHER INFORMATION: a,g,c or t
<220> FEATURE:
<221> NAME/KEY: variation
<222> LOCATION: (771)
<223> OTHER INFORMATION: a,g,c or t
<220> FEATURE:
<221> NAME/KEY: variation
<222> LOCATION: (780)
<223> OTHER INFORMATION: a,g,c or t
<220> FEATURE:
<221> NAME/KEY: variation
<222> LOCATION: (783)
<223> OTHER INFORMATION: a,g,c or t
<220> FEATURE:
<221> NAME/KEY: variation
<222> LOCATION: (789)
<223> OTHER INFORMATION: a,g,c or t
<220> FEATURE:
<221> NAME/KEY: variation
<222> LOCATION: (792)
<223> OTHER INFORMATION: a,g,c or t
<220> FEATURE:
<221> NAME/KEY: variation
<222> LOCATION: (804)
<223> OTHER INFORMATION: a,g,c or t
<220> FEATURE:
<221> NAME/KEY: variation
<222> LOCATION: (807)
<223> OTHER INFORMATION: a,g,c or t
<220> FEATURE:
<221> NAME/KEY: variation
<222> LOCATION: (810)
<223> OTHER INFORMATION: a,g,c or t
<220> FEATURE:
<221> NAME/KEY: variation
<222> LOCATION: (813)
<223> OTHER INFORMATION: a,g,c or t
<220> FEATURE:
<221> NAME/KEY: variation
<222> LOCATION: (816)
<223> OTHER INFORMATION: a,g,c or t
<220> FEATURE:
<221> NAME/KEY: variation
<222> LOCATION: (819)
<223> OTHER INFORMATION: a,g,c or t
<220> FEATURE:
<221> NAME/KEY: variation
<222> LOCATION: (822)
<223> OTHER INFORMATION: a,g,c or t
<220> FEATURE:
<221> NAME/KEY: variation
<222> LOCATION: (825)
<223> OTHER INFORMATION: a,g,c or t
<220> FEATURE:
<221> NAME/KEY: variation
<222> LOCATION: (828)
<223> OTHER INFORMATION: a,g,c or t
<220> FEATURE:
<221> NAME/KEY: variation
<222> LOCATION: (831)
<223> OTHER INFORMATION: a,g,c or t
<220> FEATURE:
<221> NAME/KEY: variation
<222> LOCATION: (834)
<223> OTHER INFORMATION: a,g,c or t
<220> FEATURE:
<221> NAME/KEY: variation
<222> LOCATION: (837)
<223> OTHER INFORMATION: a,c,g or t
<220> FEATURE:
<221> NAME/KEY: variation
<222> LOCATION: (840)
<223> OTHER INFORMATION: a,g,c or t
<220> FEATURE:
```

```
<221> NAME/KEY: variation
<222> LOCATION: (846)
<223> OTHER INFORMATION: a,g,c or t
<220> FEATURE:
<221> NAME/KEY: variation
<222> LOCATION: (849)
<223> OTHER INFORMATION: a,g,c or t
<220> FEATURE:
<221> NAME/KEY: variation
<222> LOCATION: (855)
<223> OTHER INFORMATION: a,g,c or t
<220> FEATURE:
<221> NAME/KEY: variation
<222> LOCATION: (861)
<223> OTHER INFORMATION: a,g,c or t
<220> FEATURE:
<221> NAME/KEY: variation
<222> LOCATION: (867)
<223> OTHER INFORMATION: a,g,c or t
<220> FEATURE:
<221> NAME/KEY: variation
<222> LOCATION: (870)
<223> OTHER INFORMATION: a,g,c or t
<220> FEATURE:
<221> NAME/KEY: variation
<222> LOCATION: (873)
<223> OTHER INFORMATION: a,g,c or t
<220> FEATURE:
<221> NAME/KEY: variation
<222> LOCATION: (879)
<223> OTHER INFORMATION: a,g,c or t
<220> FEATURE:
<221> NAME/KEY: variation
<222> LOCATION: (888)
<223> OTHER INFORMATION: a,g,c or t
<220> FEATURE:
<221> NAME/KEY: variation
<222> LOCATION: (891)
<223> OTHER INFORMATION: a,g,c or t
<220> FEATURE:
<221> NAME/KEY: variation
<222> LOCATION: (894)
<223> OTHER INFORMATION: a,g,c or t
<220> FEATURE:
<221> NAME/KEY: variation
<222> LOCATION: (897)
<223> OTHER INFORMATION: a,g,c or t
<220> FEATURE:
<221> NAME/KEY: variation
<222> LOCATION: (903)
<223> OTHER INFORMATION: a,g,c or t
<220> FEATURE:
<221> NAME/KEY: variation
<222> LOCATION: (906)
<223> OTHER INFORMATION: a,g,c or t
<220> FEATURE:
<221> NAME/KEY: variation
<222> LOCATION: (912)
<223> OTHER INFORMATION: a,g,c or t
<220> FEATURE:
<221> NAME/KEY: variation
<222> LOCATION: (915)
<223> OTHER INFORMATION: a,g,c or t
<220> FEATURE:
<221> NAME/KEY: variation
<222> LOCATION: (924)
<223> OTHER INFORMATION: a,g,c or t
<220> FEATURE:
<221> NAME/KEY: variation
<222> LOCATION: (930)
<223> OTHER INFORMATION: a,g,c or t
<220> FEATURE:
<221> NAME/KEY: variation
<222> LOCATION: (936)
<223> OTHER INFORMATION: a,g,c or t
<220> FEATURE:
<221> NAME/KEY: variation
<222> LOCATION: (939)
<223> OTHER INFORMATION: a,g,c or t
```

```
<220> FEATURE:
<221> NAME/KEY: variation
<222> LOCATION: (942)
<223> OTHER INFORMATION: a,c,g or t
<220> FEATURE:
<221> NAME/KEY: variation
<222> LOCATION: (948)
<223> OTHER INFORMATION: a,g,c or t
<220> FEATURE:
<221> NAME/KEY: variation
<222> LOCATION: (951)
<223> OTHER INFORMATION: a,g,c or t
<220> FEATURE:
<221> NAME/KEY: variation
<222> LOCATION: (954)
<223> OTHER INFORMATION: a,g,c or t
<220> FEATURE:
<221> NAME/KEY: variation
<222> LOCATION: (957)
<223> OTHER INFORMATION: a,g,c or t
<220> FEATURE:
<221> NAME/KEY: variation
<222> LOCATION: (960)
<223> OTHER INFORMATION: a,g,c or t
<220> FEATURE:
<221> NAME/KEY: variation
<222> LOCATION: (966)
<223> OTHER INFORMATION: a,g,c or t
<220> FEATURE:
<221> NAME/KEY: variation
<222> LOCATION: (972)
<223> OTHER INFORMATION: a,g,c or t
<220> FEATURE:
<221> NAME/KEY: variation
<222> LOCATION: (975)
<223> OTHER INFORMATION: a,g,c or t
<220> FEATURE:
<221> NAME/KEY: variation
<222> LOCATION: (978)
<223> OTHER INFORMATION: a,g,c or t
<220> FEATURE:
<221> NAME/KEY: variation
<222> LOCATION: (987)
<223> OTHER INFORMATION: a,g,c or t
<220> FEATURE:
<221> NAME/KEY: variation
<222> LOCATION: (996)
<223> OTHER INFORMATION: a,g,c or t
<220> FEATURE:
<221> NAME/KEY: variation
<222> LOCATION: (999)
<223> OTHER INFORMATION: a,g,c or t
<220> FEATURE:
<221> NAME/KEY: variation
<222> LOCATION: (1002)
<223> OTHER INFORMATION: a,g,c or t
<220> FEATURE:
<221> NAME/KEY: variation
<222> LOCATION: (1017)
<223> OTHER INFORMATION: a,g,c or t
<220> FEATURE:
<221> NAME/KEY: variation
<222> LOCATION: (1020)
<223> OTHER INFORMATION: a,g,c or t
<220> FEATURE:
<221> NAME/KEY: variation
<222> LOCATION: (1023)
<223> OTHER INFORMATION: a,g,c or t
<220> FEATURE:
<221> NAME/KEY: variation
<222> LOCATION: (1026)
<223> OTHER INFORMATION: a,g,c or t
<220> FEATURE:
<221> NAME/KEY: variation
<222> LOCATION: (1029)
<223> OTHER INFORMATION: a,g,c or t
<220> FEATURE:
<221> NAME/KEY: variation
<222> LOCATION: (1032)
```

```
<223> OTHER INFORMATION: a,g,c or t
<220> FEATURE:
<221> NAME/KEY: variation
<222> LOCATION: (1035)
<223> OTHER INFORMATION: a,g,c or t
<220> FEATURE:
<221> NAME/KEY: variation
<222> LOCATION: (1038)
<223> OTHER INFORMATION: a,g,c or t
<220> FEATURE:
<221> NAME/KEY: variation
<222> LOCATION: (1050)
<223> OTHER INFORMATION: a,g,c or t
<220> FEATURE:
<221> NAME/KEY: variation
<222> LOCATION: (1053)
<223> OTHER INFORMATION: a,g,c or t
<220> FEATURE:
<221> NAME/KEY: variation
<222> LOCATION: (1056)
<223> OTHER INFORMATION: a,g,c or t
<220> FEATURE:
<221> NAME/KEY: variation
<222> LOCATION: (1059)
<223> OTHER INFORMATION: a,g,c or t
<220> FEATURE:
<221> NAME/KEY: variation
<222> LOCATION: (1062)
<223> OTHER INFORMATION: a,c,g or t
<220> FEATURE:
<221> NAME/KEY: variation
<222> LOCATION: (1065)
<223> OTHER INFORMATION: a,g,c or t
<220> FEATURE:
<221> NAME/KEY: variation
<222> LOCATION: (1068)
<223> OTHER INFORMATION: a,g,c or t
<220> FEATURE:
<221> NAME/KEY: variation
<222> LOCATION: (1071)
<223> OTHER INFORMATION: a,g,c or t
<220> FEATURE:
<221> NAME/KEY: variation
<222> LOCATION: (1074)
<223> OTHER INFORMATION: a,g,c or t
<220> FEATURE:
<221> NAME/KEY: variation
<222> LOCATION: (1080)
<223> OTHER INFORMATION: a,g,c or t
<220> FEATURE:
<221> NAME/KEY: variation
<222> LOCATION: (1086)
<223> OTHER INFORMATION: a,g,c or t
<220> FEATURE:
<221> NAME/KEY: variation
<222> LOCATION: (1092)
<223> OTHER INFORMATION: a,g,c or t
<220> FEATURE:
<221> NAME/KEY: variation
<222> LOCATION: (1101)
<223> OTHER INFORMATION: a,g,c or t
<220> FEATURE:
<221> NAME/KEY: variation
<222> LOCATION: (1107)
<223> OTHER INFORMATION: a,g,c or t
<220> FEATURE:
<221> NAME/KEY: variation
<222> LOCATION: (1110)
<223> OTHER INFORMATION: a,g,c or t
<220> FEATURE:
<221> NAME/KEY: variation
<222> LOCATION: (1116)
<223> OTHER INFORMATION: a,g,c or t
<220> FEATURE:
<221> NAME/KEY: variation
<222> LOCATION: (1119)
<223> OTHER INFORMATION: a,g,c or t
<220> FEATURE:
<221> NAME/KEY: variation
```

```
<222> LOCATION: (1125)
<223> OTHER INFORMATION: a,g,c or t
<220> FEATURE:
<221> NAME/KEY: variation
<222> LOCATION: (1131)
<223> OTHER INFORMATION: a,g,c or t
<220> FEATURE:
<221> NAME/KEY: variation
<222> LOCATION: (1134)
<223> OTHER INFORMATION: a,g,c or t
<220> FEATURE:
<221> NAME/KEY: variation
<222> LOCATION: (1140)
<223> OTHER INFORMATION: a,g,c or t
<220> FEATURE:
<221> NAME/KEY: variation
<222> LOCATION: (1149)
<223> OTHER INFORMATION: a,g,c or t
<220> FEATURE:
<221> NAME/KEY: variation
<222> LOCATION: (1152)
<223> OTHER INFORMATION: a,g,c or t
<220> FEATURE:
<221> NAME/KEY: variation
<222> LOCATION: (1155)
<223> OTHER INFORMATION: a,g,c or t
<220> FEATURE:
<221> NAME/KEY: variation
<222> LOCATION: (1164)
<223> OTHER INFORMATION: a,g,c or t
<220> FEATURE:
<221> NAME/KEY: variation
<222> LOCATION: (1167)
<223> OTHER INFORMATION: a,g,c or t
<220> FEATURE:
<221> NAME/KEY: variation
<222> LOCATION: (1170)
<223> OTHER INFORMATION: a,g,c or t
<220> FEATURE:
<221> NAME/KEY: variation
<222> LOCATION: (1176)
<223> OTHER INFORMATION: a,g,c or t
<220> FEATURE:
<221> NAME/KEY: variation
<222> LOCATION: (1182)
<223> OTHER INFORMATION: a,g,c or t
<220> FEATURE:
<221> NAME/KEY: variation
<222> LOCATION: (1188)
<223> OTHER INFORMATION: a,g,c or t
<220> FEATURE:
<221> NAME/KEY: variation
<222> LOCATION: (1194)
<223> OTHER INFORMATION: a,c,g or t
<220> FEATURE:
<221> NAME/KEY: variation
<222> LOCATION: (1206)
<223> OTHER INFORMATION: a,g,c or t
<220> FEATURE:
<221> NAME/KEY: variation
<222> LOCATION: (1209)
<223> OTHER INFORMATION: a,g,c or t
<220> FEATURE:
<221> NAME/KEY: variation
<222> LOCATION: (1212)
<223> OTHER INFORMATION: a,g,c or t
<220> FEATURE:
<221> NAME/KEY: variation
<222> LOCATION: (1215)
<223> OTHER INFORMATION: a,g,c or t
<220> FEATURE:
<221> NAME/KEY: variation
<222> LOCATION: (1218)
<223> OTHER INFORMATION: a,g,c or t
<220> FEATURE:
<221> NAME/KEY: variation
<222> LOCATION: (1224)
<223> OTHER INFORMATION: a,g,c or t
<220> FEATURE:
```

```
<221> NAME/KEY: variation
<222> LOCATION: (1236)
<223> OTHER INFORMATION: a,g,c or t
<220> FEATURE:
<221> NAME/KEY: variation
<222> LOCATION: (1239)
<223> OTHER INFORMATION: a,g,c or t
<220> FEATURE:
<221> NAME/KEY: variation
<222> LOCATION: (1242)
<223> OTHER INFORMATION: a,g,c or t
<220> FEATURE:
<221> NAME/KEY: variation
<222> LOCATION: (1251)
<223> OTHER INFORMATION: a,g,c or t
<220> FEATURE:
<221> NAME/KEY: variation
<222> LOCATION: (1257)
<223> OTHER INFORMATION: a,g,c or t
<220> FEATURE:
<221> NAME/KEY: variation
<222> LOCATION: (1263)
<223> OTHER INFORMATION: a,g,c or t
<220> FEATURE:
<221> NAME/KEY: variation
<222> LOCATION: (1266)
<223> OTHER INFORMATION: a,g,c or t
<220> FEATURE:
<221> NAME/KEY: variation
<222> LOCATION: (1275)
<223> OTHER INFORMATION: a,g,c or t
<220> FEATURE:
<221> NAME/KEY: variation
<222> LOCATION: (1278)
<223> OTHER INFORMATION: a,g,c or t
<220> FEATURE:
<221> NAME/KEY: variation
<222> LOCATION: (1281)
<223> OTHER INFORMATION: a,g,c or t
<220> FEATURE:
<221> NAME/KEY: variation
<222> LOCATION: (1284)
<223> OTHER INFORMATION: a,g,c or t
<220> FEATURE:
<221> NAME/KEY: variation
<222> LOCATION: (1290)
<223> OTHER INFORMATION: a,g,c or t
<220> FEATURE:
<221> NAME/KEY: variation
<222> LOCATION: (1296)
<223> OTHER INFORMATION: a,g,c or t
<220> FEATURE:
<221> NAME/KEY: variation
<222> LOCATION: (1299)
<223> OTHER INFORMATION: a,g,c or t
<220> FEATURE:
<221> NAME/KEY: variation
<222> LOCATION: (1308)
<223> OTHER INFORMATION: a,g,c or t
<220> FEATURE:
<221> NAME/KEY: variation
<222> LOCATION: (1323)
<223> OTHER INFORMATION: a,g,c or t
<220> FEATURE:
<221> NAME/KEY: variation
<222> LOCATION: (1329)
<223> OTHER INFORMATION: a,g,c or t
<220> FEATURE:
<221> NAME/KEY: variation
<222> LOCATION: (1332)
<223> OTHER INFORMATION: a,g,c or t
<220> FEATURE:
<221> NAME/KEY: variation
<222> LOCATION: (1335)
<223> OTHER INFORMATION: a,g,c or t
<220> FEATURE:
<221> NAME/KEY: variation
<222> LOCATION: (1338)
<223> OTHER INFORMATION: a,c,g or t
```

```
<220> FEATURE:
<221> NAME/KEY: variation
<222> LOCATION: (1341)
<223> OTHER INFORMATION: a,g,c or t
<220> FEATURE:
<221> NAME/KEY: variation
<222> LOCATION: (1344)
<223> OTHER INFORMATION: a,g,c or t
<220> FEATURE:
<221> NAME/KEY: variation
<222> LOCATION: (1353)
<223> OTHER INFORMATION: a,g,c or t
<220> FEATURE:
<221> NAME/KEY: variation
<222> LOCATION: (1362)
<223> OTHER INFORMATION: a,g,c or t
<220> FEATURE:
<221> NAME/KEY: variation
<222> LOCATION: (1365)
<223> OTHER INFORMATION: a,g,c or t
<220> FEATURE:
<221> NAME/KEY: variation
<222> LOCATION: (1368)
<223> OTHER INFORMATION: a,g,c or t
<220> FEATURE:
<221> NAME/KEY: variation
<222> LOCATION: (1371)
<223> OTHER INFORMATION: a,g,c or t
<220> FEATURE:
<221> NAME/KEY: variation
<222> LOCATION: (1374)
<223> OTHER INFORMATION: a,g,c or t
<220> FEATURE:
<221> NAME/KEY: variation
<222> LOCATION: (1380)
<223> OTHER INFORMATION: a,g,c or t
<220> FEATURE:
<221> NAME/KEY: variation
<222> LOCATION: (1383)
<223> OTHER INFORMATION: a,g,c or t
<220> FEATURE:
<221> NAME/KEY: variation
<222> LOCATION: (1386)
<223> OTHER INFORMATION: a,g,c or t
<220> FEATURE:
<221> NAME/KEY: variation
<222> LOCATION: (1389)
<223> OTHER INFORMATION: a,g,c or t
<220> FEATURE:
<221> NAME/KEY: variation
<222> LOCATION: (1392)
<223> OTHER INFORMATION: a,g,c or t
<220> FEATURE:
<221> NAME/KEY: variation
<222> LOCATION: (1401)
<223> OTHER INFORMATION: a,g,c or t
<220> FEATURE:
<221> NAME/KEY: variation
<222> LOCATION: (1404)
<223> OTHER INFORMATION: a,g,c or t
<220> FEATURE:
<221> NAME/KEY: variation
<222> LOCATION: (1410)
<223> OTHER INFORMATION: a,g,c or t
<220> FEATURE:
<221> NAME/KEY: variation
<222> LOCATION: (1425)
<223> OTHER INFORMATION: a,g,c or t
<220> FEATURE:
<221> NAME/KEY: variation
<222> LOCATION: (1428)
<223> OTHER INFORMATION: a,g,c or t
<220> FEATURE:
<221> NAME/KEY: variation
<222> LOCATION: (1434)
<223> OTHER INFORMATION: a,g,c or t
<220> FEATURE:
<221> NAME/KEY: variation
<222> LOCATION: (1437)
```

-continued

```
<223> OTHER INFORMATION: a,g,c or t
<220> FEATURE:
<221> NAME/KEY: variation
<222> LOCATION: (1449)
<223> OTHER INFORMATION: a,g,c or t
<220> FEATURE:
<221> NAME/KEY: variation
<222> LOCATION: (1452)
<223> OTHER INFORMATION: a,g,c or t
<220> FEATURE:
<221> NAME/KEY: variation
<222> LOCATION: (1455)
<223> OTHER INFORMATION: a,g,c or t
<220> FEATURE:
<221> NAME/KEY: variation
<222> LOCATION: (1470)
<223> OTHER INFORMATION: a,g,c or t
<220> FEATURE:
<221> NAME/KEY: variation
<222> LOCATION: (1476)
<223> OTHER INFORMATION: a,g,c or t
<220> FEATURE:
<221> NAME/KEY: variation
<222> LOCATION: (1479)
<223> OTHER INFORMATION: a,c,g or t
<220> FEATURE:
<221> NAME/KEY: variation
<222> LOCATION: (1482)
<223> OTHER INFORMATION: a,g,c or t
<220> FEATURE:
<221> NAME/KEY: variation
<222> LOCATION: (1488)
<223> OTHER INFORMATION: a,g,c or t
<220> FEATURE:
<221> NAME/KEY: variation
<222> LOCATION: (1494)
<223> OTHER INFORMATION: a,g,c or t
<220> FEATURE:
<221> NAME/KEY: variation
<222> LOCATION: (1497)
<223> OTHER INFORMATION: a,g,c or t
<220> FEATURE:
<221> NAME/KEY: variation
<222> LOCATION: (1506)
<223> OTHER INFORMATION: a,g,c or t
<220> FEATURE:
<221> NAME/KEY: variation
<222> LOCATION: (1509)
<223> OTHER INFORMATION: a,g,c or t
<220> FEATURE:
<221> NAME/KEY: variation
<222> LOCATION: (1518)
<223> OTHER INFORMATION: a,g,c or t
<220> FEATURE:
<221> NAME/KEY: variation
<222> LOCATION: (1521)
<223> OTHER INFORMATION: a,g,c or t
<220> FEATURE:
<221> NAME/KEY: variation
<222> LOCATION: (1524)
<223> OTHER INFORMATION: a,g,c or t
<220> FEATURE:
<221> NAME/KEY: variation
<222> LOCATION: (1536)
<223> OTHER INFORMATION: a,g,c or t
<220> FEATURE:
<221> NAME/KEY: variation
<222> LOCATION: (1542)
<223> OTHER INFORMATION: a,g,c or t
<220> FEATURE:
<221> NAME/KEY: variation
<222> LOCATION: (1566)
<223> OTHER INFORMATION: a,g,c or t
<220> FEATURE:
<221> NAME/KEY: variation
<222> LOCATION: (1572)
<223> OTHER INFORMATION: a,g,c or t
<220> FEATURE:
<221> NAME/KEY: variation
```

<222> LOCATION: (1575)
<223> OTHER INFORMATION: a,g,c or t
<220> FEATURE:
<221> NAME/KEY: variation
<222> LOCATION: (1578)
<223> OTHER INFORMATION: a,g,c or t
<220> FEATURE:
<221> NAME/KEY: variation
<222> LOCATION: (1581)
<223> OTHER INFORMATION: a,g,c or t
<220> FEATURE:
<221> NAME/KEY: variation
<222> LOCATION: (1584)
<223> OTHER INFORMATION: a,g,c or t
<220> FEATURE:
<221> NAME/KEY: variation
<222> LOCATION: (1587)
<223> OTHER INFORMATION: a,g,c or t

<400> SEQUENCE: 10

| | | | | | |
|---|---|---|---|---|---|
| atggcngtng | tntaytayyt | nytnytngcn | ggnytnathg | cntgywsnca | ygcnytngcn | 60 |
| gcnggnacnc | cngcnytngg | ngaygaymgn | ggnmgnccnt | ggccngcnws | nytngcngcn | 120 |
| ytngcnytng | ayggnaaryt | nmgnacngay | wsnaaygcna | cngcngcngc | nwsnacngay | 180 |
| ttyggnaaya | thacnwsngc | nytnccngcn | gcngtnytnt | ayccnwsnws | nacnggngay | 240 |
| ytngtngcny | tnytnwsngc | ngcnaaywsn | acnccnggnt | ggccntayac | nathgcntty | 300 |
| mgnggnmgng | gncaywsnyt | natgggncar | gcnttygcnc | cggnggngt | ngtngtnaay | 360 |
| atggcnwsny | tnggngaygc | ngcngcnccn | ccnmgnatha | aygtnwsngc | ngayggnmgn | 420 |
| taygtngayg | cnggnggnga | rcargtntgg | athgaygtny | tnmgncnws | nytngcnmgn | 480 |
| ggngtngcnc | cnmgnwsntg | gaaygaytay | ytntayytna | cngtnggngg | nacnytnwsn | 540 |
| aaygcnggna | thwsnggnca | rgcnttymgn | cayggnccnc | arathwsnaa | ygtnytngar | 600 |
| atggaygtna | thacnggnca | yggngaratg | gtnacntgyw | snaarcaryt | naaygcngay | 660 |
| ytnttygayg | cngtnytngg | nggnytnggn | carttyggng | tnathacnmg | ngcnmgnath | 720 |
| gcngtngarc | cngcnccngc | nmgncnmgn | tgggtnmgnt | tygtntayac | ngayttygcn | 780 |
| gcnttywsng | cngaycarga | rmgnytnacn | gcnccnmgnc | cggnggngg | nggngcnwsn | 840 |
| ttyggnccna | tgwsntaygt | ngarggnwsn | gtnttygtna | aycarwsnyt | ngcnacngay | 900 |
| ytngcnaaya | cnggnttytt | yacngaygcn | gaygtngcnm | gnathgtngc | nytngcnggn | 960 |
| garmgnaayg | cnacnacngt | ntaywsnath | gargcnacny | tnaaytayga | yaaygcnacn | 1020 |
| gcngcngcng | cngcngtnga | ycargarytn | gcnwsngtny | tnggnacnyt | nwsntaygtn | 1080 |
| garggnttyg | cnttycarmg | ngaygtngcn | taygcngcnt | tyytngaymg | ngtncayggn | 1140 |
| gargargtng | cnytnaayaa | rytnggnytn | tggmgngtnc | cncayccntg | gytnaayatg | 1200 |
| ttygtnccnm | gnwsnmgnat | hgcngaytty | gaymgnggng | tnttyaargg | nathytncar | 1260 |
| ggnacngaya | thgtnggncc | nytnathgtn | tayccnytna | ayaarwsnat | gtgggaygay | 1320 |
| ggnatgwsng | cngcnacncc | nwsngargay | gtnttytayg | cngtnwsnyt | nytnttywsn | 1380 |
| wsngtngcnc | cnaaygayyt | ngcnmgnytn | cargarcara | aymgnmgnat | hytnmgntty | 1440 |
| tgygayytng | cnggnathca | rtayaaracn | tayytngcnm | gncayacnga | ymgnwsngay | 1500 |
| tgggtnmgnc | ayttyggngc | ngcnaartgg | aaymgnttyg | tngaratgaa | raayaartay | 1560 |
| gayccnaarm | gnytnytnws | nccnggncar | gayathttya | ay | | 1602 |

<210> SEQ ID NO 11
<211> LENGTH: 32
<212> TYPE: DNA

-continued

```
<213> ORGANISM: Zea mays

<400> SEQUENCE: 11
tgggaattcc atgggagat ggtgacgtgc tc                              32

<210> SEQ ID NO 12
<211> LENGTH: 33
<212> TYPE: DNA
<213> ORGANISM: Zea mays

<400> SEQUENCE: 12
gccgtcccac atggatttgt tgaggggta gac                             33

<210> SEQ ID NO 13
<211> LENGTH: 37
<212> TYPE: DNA
<213> ORGANISM: Zea mays

<400> SEQUENCE: 13
ctcaacaaat ccatgtggga cgacggcatg tcggcgg                        37

<210> SEQ ID NO 14
<211> LENGTH: 39
<212> TYPE: DNA
<213> ORGANISM: Zea mays

<400> SEQUENCE: 14
gcggtctaga tctaactaaa acatgcatgg gctatcatc                      39

<210> SEQ ID NO 15
<211> LENGTH: 33
<212> TYPE: DNA
<213> ORGANISM: Zea mays

<400> SEQUENCE: 15
atgggaattc catggggaga tggtgacgtg ctc                            33

<210> SEQ ID NO 16
<211> LENGTH: 39
<212> TYPE: DNA
<213> ORGANISM: Zea mays

<400> SEQUENCE: 16
gcggtctaga tctaactaaa acatgcatgg gctatcatc                      39

<210> SEQ ID NO 17
<211> LENGTH: 17
<212> TYPE: DNA
<213> ORGANISM: Zea mays

<400> SEQUENCE: 17
ccggttttgg taccggt                                              17

<210> SEQ ID NO 18
<211> LENGTH: 17
<212> TYPE: DNA
<213> ORGANISM: Zea mays

<400> SEQUENCE: 18
catgaccggt accaaaa                                              17

<210> SEQ ID NO 19
<211> LENGTH: 22
```

```
-continued

<212> TYPE: DNA
<213> ORGANISM: Zea mays

<400> SEQUENCE: 19
gacaccattc caagcatacc cc                                              22

<210> SEQ ID NO 20
<211> LENGTH: 22
<212> TYPE: DNA
<213> ORGANISM: Zea mays

<400> SEQUENCE: 20
gttctcacta gaaaaatgcc cc                                              22
```

CYTOKININ OXIDASE

This application claims the benefit of U.S. Provisional Application Ser. No. 60/054,268, filed Jul. 30, 1997.

BACKGROUND OF THE INVENTION

The present invention relates to a purified plant cytokinin oxidizing enzyme (ckx1) from *Zea mays*, the complete amino acid sequence of which has been elucidated, and to isolated nucleotide sequences encoding the enzyme. The invention further relates to novel methods for moderating the concentration of the enzyme and similar enzymes in plants in order to affect plant cell growth and death. Applications of the invention include the regulation of the production of ckx1 in plant roots to affect pathogenesis, the regulation to alter plant habit, and the bulk production of ckx1 enzyme for use in a plant biochemical assay.

Plant cytokinins are a class of plant hormones which, when combined with auxin, control cell division, promote shoot development from callus, release lateral buds from dormancy, and regulate plant structure and growth in a variety of ways. The naturally occurring active cytokinins in most higher plants are free-base zeatin (6-(4-hydroxy-3-methylbut-trans-2-enylamino)purine) (hereinafter Z), and its 9-riboside (hereinafter ZR). Plant tissues normally contain, therefore, Z, ZR, and smaller amounts of $N^6$-($\Delta^2$-isopentenyl)adenine (hereinafter, iP) derived from biosynthetic precursors. Elevated cytokinin levels are associated with the development of seeds in higher plants, and have been demonstrated to coincide with maximal mitotic activity in the endosperm of developing maize kernels and other cereal grains. Exogenous cytokinin application (via stem injection) has been shown to directly correlate with increased kernel yield in maize. In addition, plant cells transformed with the ipt gene from *Agrobacterium tumefaciens* (encoding a dimethylallylpyrophosphate:5'-AMP transferase capable of increasing cellular production of Z and ZR) showed increased growth corresponding to an increase in endogenous cytokinin levels upon induction of the enzyme. Thus, given the biosignificance of cytokinins to the growth of plants, the ability to manipulate cytokinin levels in higher plant cells is of great commercial and scientific interest.

The action of cytokinin oxidase is a major method of effective cytokinin catabolism in plant cells. This inactivation of cytokinin is accomplished by the oxidative removal of the side chain from cytokinin free bases (or their ribosides) in the presence of molecular oxygen. An example of this reaction with iP is shown in FIG. 1a. Although the exact chemical mechanism for this reaction is unknown, it is suspected that the enzyme is reduced during the deprotonation of iP to $N^6$-($\Delta^2$-isopentenylimino)purine. The purine is then hydrolyzed into adenine and intermediate 3-methyl-2-butenal (FIG. 1b).

While the electron acceptor responsible for reoxidizing the reduced enzyme in plant cells is not known, molecular oxygen can do so in vitro. Alternatively, the reduced enzyme may be reoxidized in vitro by intermediates such as $Cu^{+2}$/imidazole complexes or the artificial electron acceptor dichlorophenolindophenol (DCPIP).

Cytokinin oxidases are known to remove cytokinins from plant cells after cell division, and have also been postulated to be involved in the senescence process. Cytokinin oxidase activities have been shown to positively correlate to the mitosis of endosperm cells in maize kernels, along with the increase in natural cytokinin concentrations. Oxidase activity increases shortly after the increase in endogenous cytokinin levels. A similar correlation was demonstrated with artificially increased cytokinin levels in transgenic tobacco. Thus, expression of cytokinin oxidases is thought to be involved in the maintenance of hormonal homeostasis in developing plant cells. Because cytokinin oxidases appear to be substrate-inducible, they act in a negative regulatory fashion to reduce elevated cytokinin levels back to basal values. This substrate induction of cytokinin oxidase activity is a significant barrier to potential commercial applications which attempt to manipulate cytokinin levels in transgenic plants through increased cytokinin production.

Cytokinin oxidases have been discussed for a number of plant species, including *Vinca rosea*, beans (*Phaseolus vulgaris* and *lunatus*), wheat (*Triticum aestivum*), tobacco (*Nicotiana tabacum*), *Dianthus caryophyllus*, soy (*Glycine max*), and maize (*Zea mays*). All of these plant cytokinin oxidases have a similar substrate preference for iP and Z, but show limited or no reactivity with bulky, reduced, or aromatic side chain cytokinins. All also exhibit enhanced activity in the presence of copper plus imidazole. However, these enzymes show substantial variation in both specific activity and molecular weight. This is thought to be linked to the occurrence of glycosylated and unglycosylated variants of the protein, both between and within species.

In the case of the glycosylated cytokinin oxidase, the heavily glycosylated protein may present a carbohydrate-rich surface, preventing antibody formation against peptide epitopes. The glyco-epitopes to which antibodies are raised under these conditions are non-specific, and may prevent isolation of the protein, or clones containing the gene which encodes it, via immuno-chromatography or other immunology-based means. An earlier reported attempt to isolate the gene for maize cytokinin oxidase (ckx1) by immunoscreening of maize cDNA library expression products (Burch, 1992) was unsuccessful.

As demonstrated, the full amino acid sequence and encoding DNA for a cytokinin oxidase has been a long sought after goal in modern plant physiology.

SUMMARY OF THE INVENTION

It is therefore an object of the present invention to provide a means by which recombinant cytokinin oxidase may be produced in quantity so that the effects of cytokinin oxidase on plant growth and metabolism may be studied. It is also an object of the present invention to provide a means for the modification of cytokinin oxidase production in plant cells, in vivo, in order to modulate the endogenous cytokinin level of plant cells to effect altered pathogen resistance and plant growth properties.

The present invention, therefore, is directed to a novel, isolated and substantially purified plant cytokinin oxidizing enzyme, (ckx1), having a molecular weight most preferably of about 60 kD, a sequence length of from about 505 to 565 amino acid residues, preferably 525 to 545 amino acid residues, and most preferably 534 amino acid residues, and having cytokinin inactivating activity. The present invention is also directed to a protein having an amino acid sequence which includes the amino acid sequence of ckx1 (SEQ. ID NO. 1). The invention is directed as well to a protein which has cytokinin inactivating activity and which includes a portion of the amino acid sequence of ckx1 at least about 20 amino acid residues in length, where the included portion of the ckx1 sequence confers the cytokinin inactivating activity on the protein. The invention is directed to proteins which have cytokinin inactivating activity and have at least about 65% sequence identity to ckx1 and most preferably at least about 95% sequence identity to ckx1, with the remaining amino acids being conservatively substituted.

The invention is directed, moreover, to substantially isolated nucleic acid polymers encoding ckx1 or a cytokinin oxidizing homolog thereof. The nucleic acid polymer most preferably has a nucleic acid sequence of SEQ. ID NO. 3 or the predictable variants thereof described in SEQ. ID NO. 10. The invention is also directed to a substantially isolated nucleic acid polymer which contains a portion of SEQ. ID NO. 2, SEQ. ID NO. 3, or a nucleic acid polymer described by SEQ. ID NO. 10, the portion being at least 60 bp in length. In addition, the invention is directed to nucleic acid polymers which are able to hybridize with SEQ. ID NO. 2, SEQ. ID NO. 3, or a nucleic acid polymer described by SEQ ID NO. 10, under conditions of 0.5× to 2× SSC buffer, 0.1% SDS, and a temperature of 55–65° C. Nucleic acid polymers which encode cytokinin oxidases and meet the above requirements encode proteins of sufficient similarity to ckx1 to be generally recognized as equivalents of ckx1 among those skilled in the biochemical arts.

The invention is also directed to a host cell incorporating a vector containing the aforementioned DNA, and to a method for producing ckx1 or a homolog thereof using such a host cell. The method preferably comprises first ligating DNA encoding the aforementioned ckx1 or a segment or homolog thereof and an appropriate promoter (such as the RB7 root-specific promoter, Conkling, M. A., et al., U.S. Pat. No. 5,459,252; or CaMV35S promotor, Odell, 1985), or a combination of promoters (Hoffman, U.S. Pat. No. 5,106,739) 3) into an appropriate DNA vector (for instance, pBIN19 for use in *Agrobacterium tumefaciens*). The vector construct may then be directly transformed into a host cell, such as *Pichia pastoris* (described in Example 2). It may also be incorporated into a secondary vector for transformation into a host cell, such as *Agrobacterium tumefaciens*, and transformed into a plant cell host (described in Example 4 with *Nicotiana tabacum*).

Alternatively, for production of larger amounts of the enzyme, the DNA encoding ckx1, or a portion thereof, may be transformed into Pichia, according to the methods described in Example 2, or in Su, et al., 1996 and Skory, et al., 1996. When transformed into Pichia spp., ckx1 is secreted into the culture medium because of the presence of a secretory signal peptide at the N-terminus of the ckx1 coding region. Thus, active enzyme may be readily purified from bulk Pichia cultures without a lysing step. ckx1 produced in such a manner may be used in a biochemical assay to determine unknown concentrations of cytokinin in biological samples, according to the method of Example 3.

A plant host cell generated by the above method may be regenerated into an entire plant. Depending on the promoter used in the vector construct, ckx1 may be produced constitutively or by induction through natural or artificial environment factors. Plants transformed specific promoters and a sequence encoding ckx1 can exhibit altered resistance to certain cytokinin-linked plant pathologies, such as infection by certain nematodal or fungal species.

The discoveries described herein provide an important analytical tool for, and a critical link in, the development of methods by which the manipulation of cytokinin oxidase activity may be used to either inhibit or enhance a variety of cell growth functions in plants in a desired manner. Possible uses include the development of commercial plants with increased grain production, disease resistance, or with more desirable secondary growth characteristics. The enzyme and its encoding nucleic acids have important uses in the study of plant cell growth cycles and senescence. In addition, many other pharmaceutical and agricultural uses for ckx1 and its gene may be discovered. The enzyme, methods of expressing the enzyme, and methods for its use are described in greater detail below.

Other features and objects of the present invention will be in part apparent to those skilled in the art and in part pointed out hereinafter.

BRIEF DESCRIPTION OF THE FIGURES, SEQUENCE IDENTIFICATIONS, AND DEFINITIONS

The invention is further disclosed and illustrated by the accompanying figures.

FIGS. 1*a* & *b* show an exemplary reaction catalyzed by cytokinin oxidase (Brownlee, 1975), and its putative mechanism as described above, based on Hare, 1994.

FIG. 11 is a diagram of DNA plasmid pROM28.

FIG. 12 is a diagram of DNA plasmid pROM29.

FIG. 13 is a diagram of DNA plasmid pROM30.

Figure 1A:
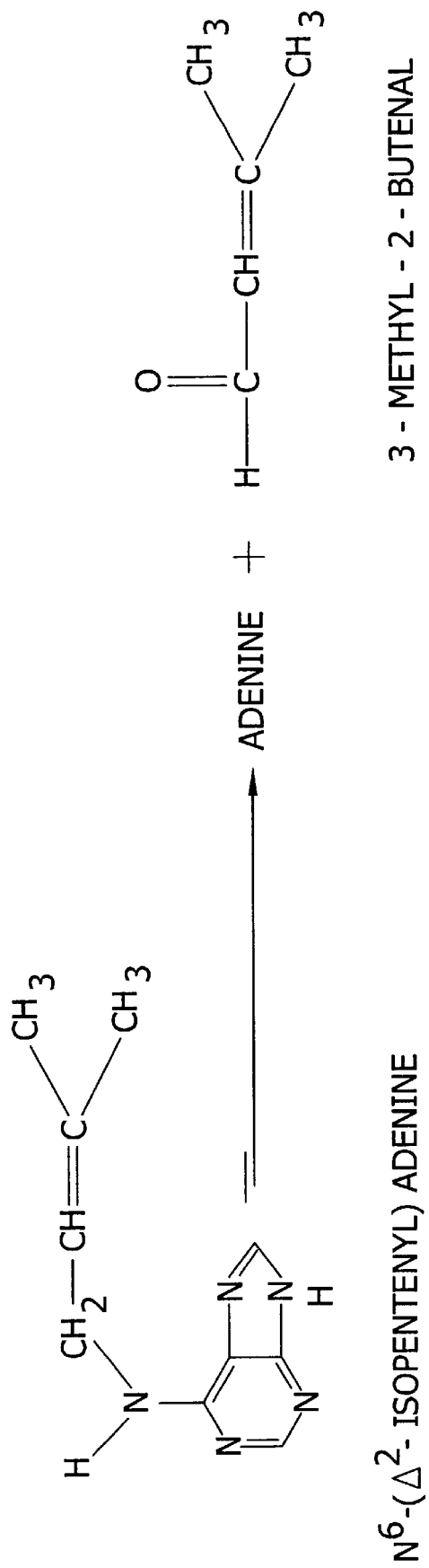

All Sequence Identification abbreviations of amino acids and nucleotides conform to USPTO and WIPO standards.

SEQ. ID NO. 1 lists the amino acid sequence of naturally occurring ckx1 derived from *Zea mays*. This sequence was predicted from the genomic DNA derived nucleotide sequence encoding ckx1.

SEQ. ID NO. 2 lists the genomic DNA sequence encoding ckx1, including introns.

SEQ. ID NO. 3 lists the coding DNA sequence for ckx1, with introns excluded. This sequence has been reconstructed in pROM22 of Example 2.

SEQ. ID NO. 4 lists the amino acid sequence of an internal tryptic digest fragment of ckx1.

SEQ. ID NO. 5 lists the amino acid sequence of an internal tryptic digest fragment of ckx1.

SEQ. ID NO. 6 lists the nucleic acid sequence of a degenerate DNA probe used to isolate the genomic DNA encoding ckx1, as described in Example 1. Note that the residues designated "n" in the sequence are the artificial base inosine (I). Normal conventions have been followed for the indication of degeneracies in the sequence.

SEQ. ID NO. 7 lists the nucleic acid sequence of a degenerate DNA probe used to isolate the genomic DNA encoding ckx1, as described in Example 1. Note that the residues designated "n" in the sequence are the artificial base inosine (I). Normal conventions have been followed for the indication of degeneracies in the sequence.

SEQ. ID NO. 8 lists the nucleic acid sequence of a degenerate DNA probe used to isolate the genomic DNA encoding ckx1, as described in Example 1. Note that the residues designated "n" in the sequence are the artificial base inosine (I). Normal conventions have been followed for the indication of degeneracies in the sequence.

SEQ. ID NO. 9 lists the nucleic acid sequence of a degenerate DNA probe used to isolate the genomic DNA encoding ckx1, as described in Example 1. Note that the residues designated "n" in the sequence are the artificial base inosine (I). Normal conventions have been followed for the indication of degeneracies in the sequence.

SEQ. ID NO. 10 lists the degenerate DNA sequence encoding ckx1. As is well known in the art, the several DNA molecules indicated by this group encode a protein with the amino acid sequence of SEQ. ID NO. 1, also known as ckx1. This group follows the conventional rules of degeneracy in the genetic code. Special modifications necessary for expression in certain organisms which do not follow these conventions could easily be made by an individual of ordinary skill in the art.

SEQ. ID NO. 11 lists the sequence of a synthetic primer used in the PCR removal of introns in example 2.

SEQ. ID NO. 12 lists the sequence of a synthetic primer used in the PCR removal of introns in example 2.

SEQ. ID NO. 13 lists the sequence of a synthetic primer used in the PCR removal of introns in example 2.

SEQ. ID NO. 14 lists the sequence of a synthetic primer used in the PCR removal of introns in example 2.

SEQ. ID NO. 15 lists the sequence of a synthetic primer used in the PCR removal of introns in example 2.

SEQ. ID NO. 16 lists the sequence of a synthetic primer used in the PCR removal of introns in example 2.

SEQ. ID NO. 17 lists the sequence of a synthetic linker construct used in example 2.

SEQ. ID NO. 18 lists the sequence of a synthetic linker construct used in example 2.

SEQ. ID NO. 19 lists the sequence of a synthetic primer used in PCR to obtain the tobacco RB7 promoter in example 4.

SEQ. ID NO. 20 lists the sequence of a synthetic primer used in PCR to obtain the tobacco RB7 promoter in example 4.

As used herein, a "substantially purified protein" means that the protein is separated from a majority of host cell proteins normally associated with it or that the protein is synthesized in substantially purified form, such synthesis including expression of the protein in a host cell from a nucleic acid polymer exogenously introduced into the cell by any suitable gene-therapy delivery means.

A "substantially isolated nucleic acid polymer" means that the mixture which comprises the nucleic acid polymer of interest is essentially free of a majority of other nucleic acid polymers normally associated with it. A "nucleic acid polymer" includes a polymer of nucleotides or nucleotide derivatives or analogs, including for example deoxyribonucleotides, ribonucleotides, etc. Genomic DNA, cDNA and mRNA are exemplary nucleic acid polymers.

The terms "regulate transcription," "modify transcription," "regulate production," and "modify production," is intended to include promotion and/or repression of transcription or mRNA or production/translation of a protein.

The term "expression regulatory sequence" means a nucleic acid polymer sequence ligated to a protein encoding sequence which, when introduced into a host cell, either induces or prevents expression of that protein. These sequences may or may not also encode proteins used in their regulatory mechanism. Examples of expression regulatory sequences include the CaMV promoter, the ocs terminator, and the tet operator sequences.

The term "gene" is intended to include both endogenous and heterologous genes, and specifically, both genomic DNA which encodes a target protein in a naturally occurring cell, and also cDNA encoding the target protein, for example, wherein the cDNA is a part of a nucleic acid construct such as a plasmid vector or virus which has been introduced into a cell or a cDNA produced by RT-PCR.

The term "vector" is intended to include any physical or biochemical vehicle containing nucleic acid polymers of interest, by which those nucleic acid polymers are transferred into a host cell, thereby transforming that cell with the introduced nucleic acid polymers. Examples of vectors include DNA plasmids, viruses, particle gun pellets, and bacteria such as *Agrobacterium tumefaciens*. The term "primary vector" is intended to mean the first vector used in a transformation series, either as one step (e.g. a plasmid used to transform a yeast cell), or with a "secondary vector" (e.g. a plasmid used to transform *Agrobacterium tumefaciens*, which is later used to transform a plant cell).

The term "host cell" is intended to mean the target cell for vector transformation, in which the transferred nucleic acid polymer will be replicated and/or expressed.

The term "conservative substitution," in the context of amino acid sequences, means the substitution of one amino acid in the sequence with another with a side chain of similar size and charge. An example of a conservative substitution would be substituting glutamine for asparagine. Conservative substitutions in a protein sequence which would be expected to have minimal to no impact on protein structure or function can be readily devised by a person of ordinary skill in the biochemical arts.

The term "plant products" means any cellular material produced by a plant, especially those which may be used for propagation of the plant. Plant products include seeds, rhizomes, leaves, meristem, roots, and buds.

The term "SSC buffer" means a solution of 8.765 g NaCl and 4.41 g sodium citrate in 1 liter of water, pH adjusted to 7.0 by titrimetric addition of 10 N NaOH solution.

The contents of each of the references cited herein are being incorporated by reference in their entirety.

DETAILED DESCRIPTION OF THE INVENTION

The present invention relates to newly sequenced cytokinin oxidase isolated from the maize plant, *Zea mays*, designated ckx1, which exhibits a substrate specific cytokinin oxidizing activity. The enzyme has been linked to the development and maturation of kernels in maize, as well as the senescence of plant tissues. The control of these plant functions appears to be achieved by the degradation of endogenous and exogenous cytokinin concentrations. Because ckx1 efficiently oxidizes unsaturated-side-chain free cytokinins and their ribosides, such as iP, Z, and ZR (which also induce production of the enzyme when applied exogenously or endogenously), it is thought that ckx1 rigorously controls the availability of these active cytokinins as a part of plant growth regulation.

During the course of developing the claimed invention, the applicant encountered several difficulties which may explain why the search for a cytokinin oxidase gene has been heretofore unsuccessful. The protein is expressed at very low levels, and only at certain periods of the plant growth cycle. Therefore, screening a λ-cDNA maize library in *E. coli* may not yield ckx1 simply because the gene was not expressed, or not expressed in detectable amounts, when the library was taken. Also, isolation of the protein may have been a problem for some researchers, since its active form does not survive gel filtration. Only through the development of his own screening process, described in Example 1, was the applicant able to isolate the protein in sufficient purity for tryptic digestion and subsequent sequencing.

Even after the protein was purified, obtaining the gene sequence for ckx1 proved to be difficult. Apparently, the N-terminal end of ckx1 is blocked, so a straightforward Edman degradation determination of its N-terminal sequence was impossible. Only small, internal sequences were determinable after tryptic digestion of the protein, SEQ. ID NO. 4 & 5. Because the location of these fragments in the protein's amino acid sequence was unknown, several problems had to be overcome in order to successfully probe the *Zea mays* genome for the ckx1 gene, as detailed in Example 1. The small size of the sequenced peptides necessitated using a "bookended" criteria (one probe at either end of the replicated DNA) in order to eliminate non-ckx1 DNA from either side of the ckx1 gene. One could be reasonably certain that the DNA between two probes would be part of the ckx1 gene. A hybridization/amplification product size criteria of 300 bp was also necessary in order to distinguish between dimerized degenerate primers and PCR products. A simple degenerate strategy was unlikely to work because of the high degeneracy inherent in the particular amino acid sequences available from the tryptic peptides. Initially, when a standard degenerate nucleotide strategy was used, utilizing all possible oligonucleotides encoding the interior amino acid sequences, the low concentration of specifically binding primer was not sufficient for the initiation of PCR amplification. The applicant was able to overcome this problem only by using inosine containing degenerate probes with a broader specificity. Also, several of the degenerate probes were too close together to yield products of the target size, or not in the right order in the gene to produce "bookended" products. Only probes SEQ ID NO. 6, 7, 8, & 9 proved to be of use in isolating the ckx1 gene.

The identity of the isolated gene was verified by two independent methods. First, it was verified by testing the affinity of goat antisera to an *Escherichia coli* produced translation of SEQ. ID NO. 3 for ckx1 in maize kernel extracts, as per Example 1. Second, it was confirmed by expressing SEQ. ID No. 3 in *Pichia pastoris* resulting in the secretion of active cytokinin oxidase as per Example 2.

SEQ. ID NO. 2 lists the complete genomic DNA sequence of ckx1, which yields the glycosylated form of the protein when expressed in *Zea mays*. The predicted location of the introns in the genomic sequence was verified using the reverse transcriptase-polymerase chain reaction to find the actual transcribed length of RNA, as per Example 1. SEQ. ID NO. 3 lists the coding DNA sequence for ckx1, which yields the amino acid sequence set forth in SEQ. ID NO. 1.

The state of the art of molecular biology is now sufficiently advanced that minor alterations can be made to a DNA sequence with relative ease and precision. A moderately skilled laboratory technician can follow the directions of one of the commercially available site-directed mutagenesis kits (for instance, the GeneEditor™ offered by Promega Corp., Madison, Wis.) to effect any number of changes to a DNA nucleotide sequence. Also well known are the general rules governing the genetic code, by which triplet nucleotide codons are translated into an amino acid sequence by standard biochemical processes. Thus, the applicant considers the group of DNA sequences denoted by the consensus sequence of SEQ. ID NO. 10, which code for the amino acid sequence of ckx1 in SEQ. ID. NO. 1, to be within the present invention. Although some variation in the genetic code and the GC % content occurs amongst some phyla, the rules governing these variations have also been well documented, and are within the reasonable skill of one versed in the molecular genetic arts. Thus, the applicant also considers any other nucleic acid sequence which encodes the amino acid sequence SEQ. ID NO. 1 to be within the scope of the present invention.

In addition, although the understanding of the field of protein biochemistry is not as complete as that of molecular genetics, the person or ordinary skill in the art of biochemistry is capable of predicting, with reasonable certainty, when certain substitutions to the primary amino acid sequence structure of a protein will not result in any appreciable modification of a protein's structure or function. Such conservative substitutions are made by replacing an amino acid in the sequence with another containing a side chain with like charge, size, and other characteristics. For instance, the amino acid alanine, which has a small nonpolar methyl side chain, generally can be replaced by glycine, an amino acid which has a small nonpolar hydrogen side chain, without any noticeable effects. Likewise, the amino acid asparagine, with a moderately bulky, polar ethamide side chain, usually can be replaced with glutamine, which has a moderately bulky, polar propamide side chain, without noticeable effects. To the extent that such conservative substitutions can be made while retaining 65%, preferably 80% or more identity to SEQ. ID NO. 1 and cytokinin oxidizing activity, such altered proteins are within the scope of the present invention.

Cytokinin oxidases are known to exist in a variety of non-glycosylated and glycosylated forms in several species of higher plants, including maize. This modification is thought to be involved in compartmentalizing cytokinin oxidases for various uses inside and outside the cell. The extent of glycosylation of the enzyme may also account for the wide variety of molecular weights observed between the cytokinin oxidases of various species. However, because substrate specificity, a requirement of molecular oxygen for activity, and copper concentration reaction rate effects in vitro are highly conserved among all higher plant cytokinin oxidases, a common domain and active site structure is believed responsible for the cytokinin oxidizing activity of all enzymes. Thus, the present invention is also directed to a protein which exhibits cytokinin oxidizing activity and which contains an amino acid sequence at least about 20 amino acids in length which is 90% identical (or would be identical with conservative amino acid substitutions) to a similarly sized portion of SEQ. ID NO. 1.

Another object of the current invention is the regulated production of ckx1 in various host cells, either for later bulk isolation, or regulated intracellular production. For instance, ckx1 may be produced in unglycosylated form in prokaryotes, such as *E. coli*, as illustrated in example 1. More preferably, the protein may be produced in eukaryotes, as illustrated by the Pichia production of example 2. An added benefit of producing the protein in Pichia is that the protein is secreted into the culture media where it may be readily purified. Alternatively, the protein may be produced in higher eukaryotes, more preferably plants, such as the Nicotiana constructs of example 4 either as the glycosylated or non-glycosylated forms. Other examples of suitable host plant cells include *Zea mays*, *Arabidopsis thaliana*, *Brassica* spp, and *Oryza sativa*. As illustrated, ckx1 can be produced in plants either in an unregulated fashion, as shown here under the CaMV promoter, regulated by an artificial stimuli, as shown here under a tet operator combined with a CaMV promoter, and regulated by an environmental stimuli, as shown here under the RB7 promotor, which induces root-specific production of a protein in response to nematodal attack.

The several aspects of the present invention, including the ckx1 protein and the nucleic acid polymers which encode it, the cytokinin oxidizing activity of enzymes such as the ckx1 enzyme, and the regulation of cytokinin levels in plant cells by ckx1, collectively enable several practical applications, including both agricultural and research uses.

The applicant has devised an application for bulk cytokinin oxidase which greatly facilitates plant physiology research. Cytokinin oxidase can be reoxidized after oxidizing cytokinins by the synthetic oxidizing agent dichlorophenolindophenol (DCPIP). DCPIP demonstrates a reduced absorbance at 590 nm upon reduction, which can be spectrophotometrically quantified. The cytokinin concentration in a sample may be determined indirectly by measuring the decrease in oxidized DCPIP as ckx1 oxidizes the cytokinins present in the sample. More sensitive redox dyes are also available to increase the sensitivity of the assay. Therefore, it is another object of the present invention to provide a simple, fast, and effective means to assay cytokinin concentrations in a sample.

The applicant has also devised an application for the modified production of ckx1 in plants. Cytokinins are associated with several types of plant pathogenesis, including the formation of nematode feeder cells, and fungal invasion of plant tissues. Thus, the pathogen-exposure-regulated production of ckx1 can modify the efficacy of pathogenesis through cytokinin-utilizing mechanisms such as that utilized by the root-knot nematode, Meloidogyne spp. (Bird, et al., 1980), or fungal species such as *Ustilago maydis*. Thus, it is an object of the present invention to provide a method of moderating cytokinin-mediated pathogenesis by transforming a plant with a ckx1 producing DNA construct.

The following examples illustrate the principles and advantages of the invention.

EXAMPLES

Example 1
Isolation of ckx1 and characterization of its encoding sequence

Maize kernels were chosen as the raw material for purification because of the relatively high concentrations of cytokinin oxidase present about a week after pollination. Using the procedure set forth below, approximately 1.66 $\mu$g protein per kg maize yield may be obtained. Field grown maize (Pioneer 3180 or 3379) was hand pollinated, and immature ears were harvested between 5 and 8 days later (Dietrich, 1995). Kernels were harvested immediately, and frozen at −80° C. until extraction. After being powdered in liquid nitrogen, the kernels were blended in 1 kg lots with 1700 ml of Buffer A(50 mM Tris, 5 mM EDTA, ascorbic acid 0.4% w/v; 10 mM β-mercaptoethanol, pH 8.5). Acid washed PVPP (200 g wet weight, equilibrated w/Buffer A) was stirred in immediately. The slurry was filtered through Miracloth and centrifuged at 23,500× g for 15 minutes to remove debris. Polyethyleneimine solution (5% v/v, pH 8.5) was added dropwise to the centrifuged supernatant, to a final concentration of 0.05%. After recentrifugation at 23,500× g for 10 minutes, the supernatant was filtered through a 600 g pad of PVPP (prepared as above). Ammonium sulfate fractionation was performed, and the protein precipitating between 40% and 65% saturation was collected by centrifugation and dissolved in a minimum volume of Buffer B (10 mM Tris, 1 mM EDTA, 1 mM β-mercaptoethanol, pH 8.5). Insoluble material was removed by centrifugation at 35,000× g for 20 minutes. At this point, glycerol may be added to the supernatant to 10% v/v, allowing the protein to be stored at −80° C. indefinitely without loss of activity.

After dialyzing the supernatant from the ammonium sulfate fractionation against Buffer B, the fraction was applied to a DEAE-cellulose column (Whatman DE-52, 500 ml, available from the Whatman Group, Clifton, N.J.) at the rate of 10 ml/minute. After washing w/buffer B, the column was eluted with a linearly increasing concentration of KCl in Buffer B, to 200 mM over 600 ml. Protein content was measured using the Bradford dye binding assay (Bradford, 1976). Fractions were analyzed for oxidase activity as described below.

Two assays were used to screen purification steps for cytokinin oxidase activity. The first was the Schiff base formation assay measuring the production of dimethylallylaldehyde from iP, as described by Liberos-Minotta (1995), which was used up through the DEAE column step. A second assay, developed by the applicant, was used in the remaining purification steps. In this assay, the transfer of reducing equivalents from isopentenyladenine to dichlorophenolindophenol (DCPIP), catalyzed by ckx1, allows the observance of reactivity by measuring absorbance change at 590 nm. In a final volume of 250 $\mu$l, the assay contains: 100 mM Phosphate buffer, pH 7.0; 1.0 mM EDTA; 0.05 mM DCPIP; 0.1 mM iP; 100 $\mu$g/ml BSA; and the sample tested. After the addition of the enzyme, absorbance change is read at 590 nm for 10 minutes.

After purification on the DEAE column, the major pooled active material was dialyzed against Buffer C (20 mM Tris, 0.5M NaCl, 1.0 mM $CaCl_2$, pH 7.4), and applied to a concanavalin A agarose column (100 ml, from Sigma Aldrich, St. Louis, Mo.) and washed w/Buffer C (270 ml). Glycosylated proteins were eluted with a step gradient of buffer C containing α-D-methylmannoside to 1M over 400 ml. The relatively long retention time when eluted under these conditions indicates that the glycosylated form of ckx1 was isolated. Active fractions from the lectin-affinity chromatography were then dialyzed against Buffer D (10 mM Tris, 1 mM EDTA, pH 8.5) and applied to a high resolution anion exchange column (FPLC MonoQ, 1 ml, from Amersham Pharmacia Biotech, Ltd., San Francisco, Calif.), and eluted with a linear gradient of KCl to 0.12M over 24 minutes at 1 ml/minute. The active fractions from the ion exchange column were then concentrated, dialyzed against Buffer B, brought to 1.5M ammonium sulphate and applied to a hydrophobic interaction column (FPLC phenylsuperose, 1 ml, Pharmacia) equilibrated in Buffer B containing 0.6 ammonium sulfate. After washing with 0.6M ammonium sulfate for 25 minutes, the concentration of ammonium sulfate was reduced successively to 0.45M over 15 minutes and then to zero over 60 minutes.

Native gel electrophoresis was performed as illustrated in Ornstein (1964) and Davis (1964). Gels were then stained for cytokinin oxidase activity by the DCPIP procedure described above. Enzyme activity was revealed as a transparent band against a blue background. Denaturing SDS polyacrylamide gel electrophoresis was then carried out as illustrated in Laemmli (1970). When testing fractions for homogeneity, the gel was stained as described by Møller (1995). At the final purification step, the enzyme was stained with Coomassie Blue R250. The purified protein was analyzed by tryptic digestion, HPLC separation of digest, and Edman degradation sequencing of the tryptic polypeptides. Several polypeptide sequences were obtained from this analysis, including SEQ. ID NOS. 4 and 5. From these sequences, reverse translation primer probes, SEQ. ID NOS. 6,7,8, and 9, were devised, with inosine substituted at highly degenerative positions. Primers SEQ. ID NOS. 6 and 9 were then combined with maize genomic DNA, and hot-start touchdown PCR was performed (Ault, 1994) for 40 cycles. PCR products were separated on agarose gel, and an approximately 440 bp fragment was chosen to use as a hybridization probe. The identity of the fragment was confirmed by showing that it could be amplified by PCR with the nested internal primers SEQ. ID NOS. 7 and 8. The fragment amplified by the primers SEQ. ID NOS. 6 and 9 was then ligated into linearized pCRII DNA and transformed into E. coli (INVαF', Invitrogen Corp., Carlsbad, Calif.). After cloning and reisolation of DNA, plasmid inserts were sequenced using the Prism dideoxy terminator method of Applied Biosystems, Foster City, Calif., to verify that the sequenced tryptic digest polypeptides were encoded by the fragment.

Once the large fragment had been verified, it was labeled with 32p by primer extension using the Klenow fragment of DNA polymerase and primers SEQ. ID NOS. 6 and 9. Maize genomic library phage (in λ-FIXII, from Stratagene, La Jolla, Calif.) were diluted in SM Buffer, and appropriate numbers added to freshly prepared E. coli (XL1-Blue MRA (P2), Stratagene) in 10 mM $MgSO_4$ and incubated at 37° C. for 15 minutes. NZY top agar at 480C was added and the mixture plated onto NZY agar plates. After incubation for approximately 8 hours at 37° C., plates were cooled to 4° C. for 2 hours and phage were adsorbed onto sheets of Hybond N membrane (Amersham Pharmacia Biotech, San Francisco, Calif.). Membranes were air-dried for 10 minutes, and incubated successively =with 0.5M NaOH plus 1.5M NaCl, 500 ml, 5 minutes; 0.5 Tris-Cl pH 8.0 plus 1.5M NaCl, 500 ml, 5 minutes; and 2× SSC, 500 ml, 5 minutes. They were blotted dry and baked at 80° C. until dry (approximately 15 minutes). Membranes were pre-hybridized at 45° C. for less than one hour in 50% formamide, 5× SSPE, 2× Denhardt's solution, 0.2% SDS, 100–200 µg/ml denatured herring sperm or calf thymus DNA (Maniatis, 1990).

The labeled DNA fragment was then denatured at 100° C. for 5 minutes, added to the pre-hybridization solution, and hybridized for 16 hours at 45° C. For the primary screen, phage were plated at a density of 500 pfu/$cm^2$ and membranes were washed at high stringency. For subsequent plaque purification, candidate phage were plated at a density of 70 pfu/$cm^2$ and 2 pfu/$cm^2$ and membranes were washed at medium stringency. After three rounds of purification, subfragments of the insert were removed from positive phage DNA by restriction and subcloned into pBluescript (Stratagene) for characterization by restriction digestion and sequence analysis. Two overlapping plasmid subclones, pROM2 (a HindIII insert) and pROM3 (an Xho-BamHI insert) each contained part of the gene for ckx1. These overlapping sections have been fused into the plasmid clone pROM10. The plasmids pROM2, pROM3, and pROM10 have been deposited with the American Type Culture Collection as ATCC Nos. 209573, 209572, and 209571, respectively. The sequence of the cloned DNA in pROM2 and pROM3 provided the genomic sequence of ckx1, SEQ. ID NO. 2, which was verified by the inclusion of sequences coding for the tryptic digest fragments obtained above.

The location of the introns in the ckx1 gene, and the coding sequence for ckx1 (SEQ. ID NO. 3) was verified by use of the reverse transcriptase polymerase chain reaction (RT-PCR) according to the following procedure.

Total RNA(2–4 µg, DNAase I-treated) from kernels harvested five days after pollination (5 DAP) was primed for RT-PCR using oligonucleotides bracketing the intron sites. Primers 2031f (ckx1 genomic sequence 2031–2050) and XBH1 (reverse complement of ckx1 genomic sequence 2553–2570) covered the first intron site. Primers 3160f (ckx1 genomic sequence 3160–3179) and 3484r (reverse complement of ckx1 genomic sequence 3465–3484) covered the second intron site. Reverse transcription was at 50° C. for 50 min. with 200U Superscript II (Gibco-BRL) in 20 µL total volume with 25 mM Tris-Cl, pH 8.3, 37.5 mM KCl, 1.5 mM $MgCl_2$, 0.5 mM dNTPs, 5mM dithiothreitol, 40U RNAasin (Promega, Madison, Wis.). PCR was performed with 4-10% of the RT reaction product as template and 1U Taq polymerase in 1× PCR buffer (Roche Diagnostics, Basel, Switzerland), 200 µM dNTPs, and 0.5 µM each primer. Reaction conditions were: an initial denaturation at 95° C. for four minutes followed by thirty-five cycles of 950 denaturation for one minute, 60° annealing for one minute, and 72° extension for one minute. A final four minute extension was carried out at 72°. PCR products were resolved on 1.5% agarose gels. PCR products were excised from gels and sequenced to determine splice site junctions.

Figure 2A:
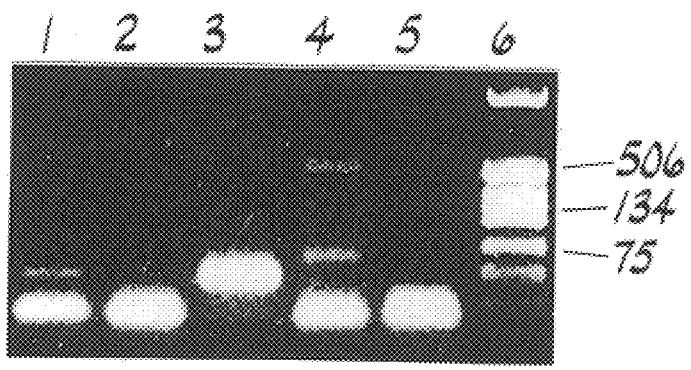
FIG. 2 shows agarose gel electrophoresis of RT-PCR DNA fragments which demonstrate that the introns of the ckx1 gene have been correctly identified.
Figure 2B:
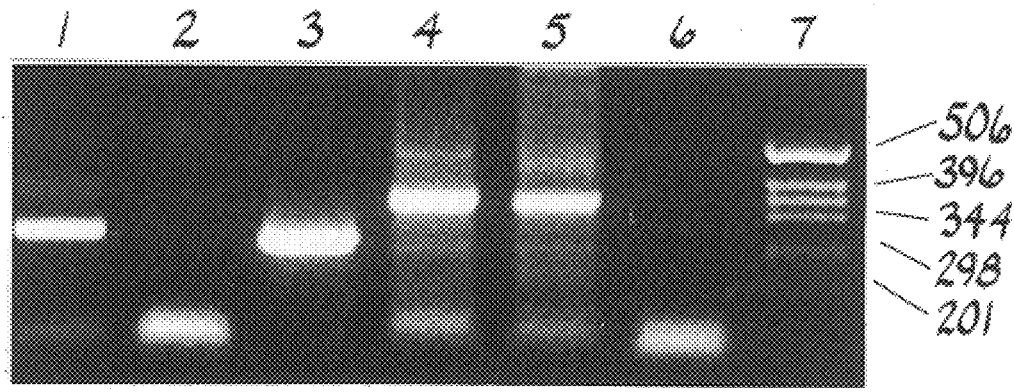

RT-PCR of maize kernel RNA (5 days after pollination) with primers designed to span the first and second intron locations demonstrated PCR product sizes consistent with splicing out of these introns in the mature oxidase mRNA. The primers bracketing the first intron should give a 539 bp product if the intron is present and a 127 bp product if it has been spliced out. Likewise, the primers bracketing the second intron should give a 324 bp product if the second intron is present and a 232 bp product if it has been spliced out. As shown in FIG. 2, the PCR products were 127 bp and 232 bp respectively, indicating that the introns had indeed been spliced out. Sequence analysis of the fragments confirmed that splicing had occurred as predicted.

The identity of the ckx1 protein and gene were further verified by the following immunological technique.

Polyclonal antibodies were raised in goats to the peptide produced by expression of a ckx1 gene fragment in E. coli. This avoided the presentation of a glycosylated surface when raising antibodies to the gene product and the problems encountered by Burch, et al., when raising antibodies to naturally occurring ckx1. Goat antibodies from immunized and unimmunized animals were partially purified by sodium sulfate precipitation (Willams, et al., 1967). Affinity columns were prepared by coupling these purified antibodies (2 mg) to Aminolink Plus gels (1 mL, Pierce) at pH 10, following the manufacturer's protocol. Activity depletion assays were performed by adding 0.2 mL (27 µg) of a maize ConA-fractioned oxidase preparation plus 0.8 mL phosphate buffered saline (PBS) to each column. The columns were capped and incubated for one hour at room temperature. Eluate was collected and assayed for cytokinin oxidase activity.

Antibodies to ckx1 recognize the major maize cytokinin oxidase enzyme. A column containing immobilized anti-ckx1-fragment antibody was able to deplete cytokinin oxidase activity from a ConA-fractionated maize extract. A control column of unimmunized goat antibodies was not able to do so.

Example 2
Expression of ckx1 in *Pichia pastoris* ckx1 protein may be produced in bulk by the following procedure for use in applications such as the cytokinin assay of Example 3, or application to plant materials.

Figure 9:
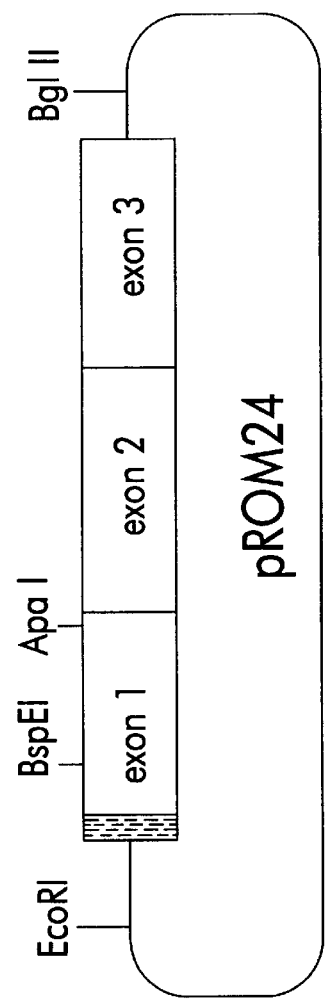
FIG. 9 is a diagram of DNA plasmid pROM24.

Expression of ckx1 in *Pichia pastoris* was carried out in four stages:

Step 1. Removal of the introns from ckx1
Step 2. Removal of the maize promoter and construction of the appropriate expression cassette using the intron-less construct
Step 3. Transformation of the final construct into Pichia and
Step 4. Expression of ckx1 in Pichia Removal of the right-most intron was accomplished by splicing by overlap extension (Horton et al., 1989) and for the left-most intron by ligation of suitable restriction fragments. The resulting intronless cassette was inserted into the Pichia expression vector pPICZ-A to give the expression construct pROM24 (FIG. 9). This construct was introduced into the requisite Pichia host and grown in the presence of methanol to induce ckx1 expression. Appropriate control Pichia lines (containing the vector alone or a recombinant expressing human serum albumin) were grown in parallel.

No cytokinin oxidase activity was observed in Pichia cell lysates containing ckx1 or the controls at any time during the growth curve. However, the Pichia line harboring ckx1 expressed and secreted high levels of cytokinin oxidase activity into the growth medium. No activity was observed in control supernatants. This provided further verification that ckx1 does indeed encode a cytokinin oxidase.

Step 1. Intron removal: The second intron (SEQ. ID NO. 2 residues 3219–3312) was removed by splicing by overlap extension with selected ckx1 restriction fragments as templates to limit artifactual priming. The following table lists the primers and templates used.

| Intron | Left Primer | Right primer | Template DNA |
| --- | --- | --- | --- |
| amplification #1 | TGGGAATTCCATGGGGAGA TGGTGACGTGCTC (SEQ. ID NO. 11) | GCCGTCCCACATGGATTTGT TGAGGGGGTAGAC (SEQ. ID NO. 12) | pROM2 Nco1/PinA1 (700 bp) fragment |
| amplification #2 | CTCAACAAATCCATGTGGG ACGACGGCATGTCGGCGG (SEQ. ID NO. 13) | GCGGTCTAGATCTAACTAAA ACATGCATGGGCTATCATC (SEQ. ID NO. 14) | pROM2 390 bp PinA1 + Vsp1 |
| amplification #3 | ATGGGAATTCCATGGGGAG ATGGTGACGTGCTC (SEQ. ID NO. 15) | GCGGTCTAGATCTAACTAAA ACATGCATGGGCTATCATC (SEQ. ID NO. 16) | Products from amplifications #1 and #2 |

Figure 8:
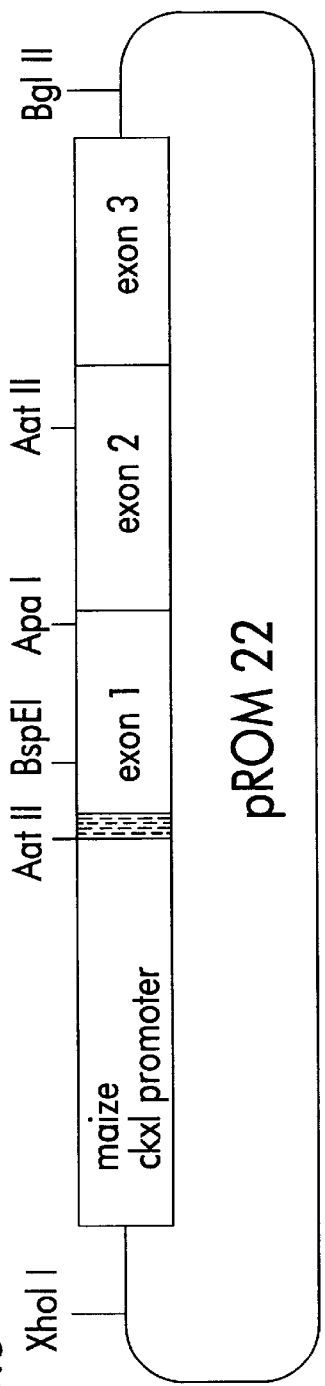
FIG. 8 is a diagram of DNA plasmid pROM22.

PCR products from reactions #1 and #2 were gel-purified and used in the final PCR step. The final product from reaction #3 was cloned and sequenced and a PflM1/Xba1 subfragment was substituted for the intron-containing PflM1/Xba1 subfragment of pROM7. The construct was designated pROM19. The first intron (SEQ. ID NO. 2 residues 2113–2524) was then removed from pROM19 by replacement of the DNA between the restriction sites PinA1 and Nco1 with a linker constructed from the oligonucleotides CCGGTTTTGGTACCGGT (SEQ. ID NO. 17) and CATGACCGGTACCAAAA (SEQ. ID NO. 18). The product was designated pROM20. Extraneous linker-associated bases were removed by digestion with PinA1 followed by re-ligation. The product, designated pROM22 (FIG. 8), contained the three fused ckx1 exons and the maize ckx1 promoter.

Step 2. The Pichia expression cassette: The maize promoter was removed by partial digestion of pROM22 (FIG. 8) with AatII, filling in the sticky ends with T4 DNA polymerase, and redigestion with BglII. The exon fusion (containing ckx1 and including its putative signal peptide) was ligated into the Pml1/BsmB1 restriction sites of pPICZ-A (Easy-Select Pichia Expression Kit version B, Invitrogen Corp.). The resulting plasmid was designated pROM24 (FIG. 9).

Step 3. Transformation into Pichia strain X33 as described in the Invitrogen protocol: The plasmid pROM24 (FIG. 9)(10 µg) was digested with Dra1 and electroporated into competent X33 cells in a 2 mM cuvette at 1.75 kV (GenePulser, Bio-Rad Laboratories, Hercules, Calif.). Selection on YPDS with 100 µg/mL zeocin resulted in many colonies. One (PPckx1) was selected for expression studies.

Step 4. Expression of the oxidase: The transformant PPckx1 was inoculated into BMGY medium (50 mL) and grown overnight. Cells were pelleted, resuspended in BMMY (containing 0.5% v/v methanol), diluted to an $A_{600}=1$ and grown at 30° C. with vigorous shaking. Additional methanol was added to 0.5% v/v at 24, 48 and 72 hours post-inoculation. Samples were harvested for assay of cytokinin oxidase activity in cell lysates or in culture supernatants. Pichia strains X33 (WT, no insert) and GS115, (secreted human serum albumin insert) served as controls.

Example 3
Use of Recombinant Cytokinin Oxidase in a Rapid Assay Method for Cytokinin Cytokinins were measured by mixing 100 µL of a buffer mixture containing phosphate buffer (250 mM, pH 7.0), EDTA (2.5 mM) and DCPIP (0.125 mM), and an excess of recombinant cytokinin oxidase with solutions (150 µL) of zeatin at various concentrations. The net change in absorbance was measured at 590 nm.

Figure 3:
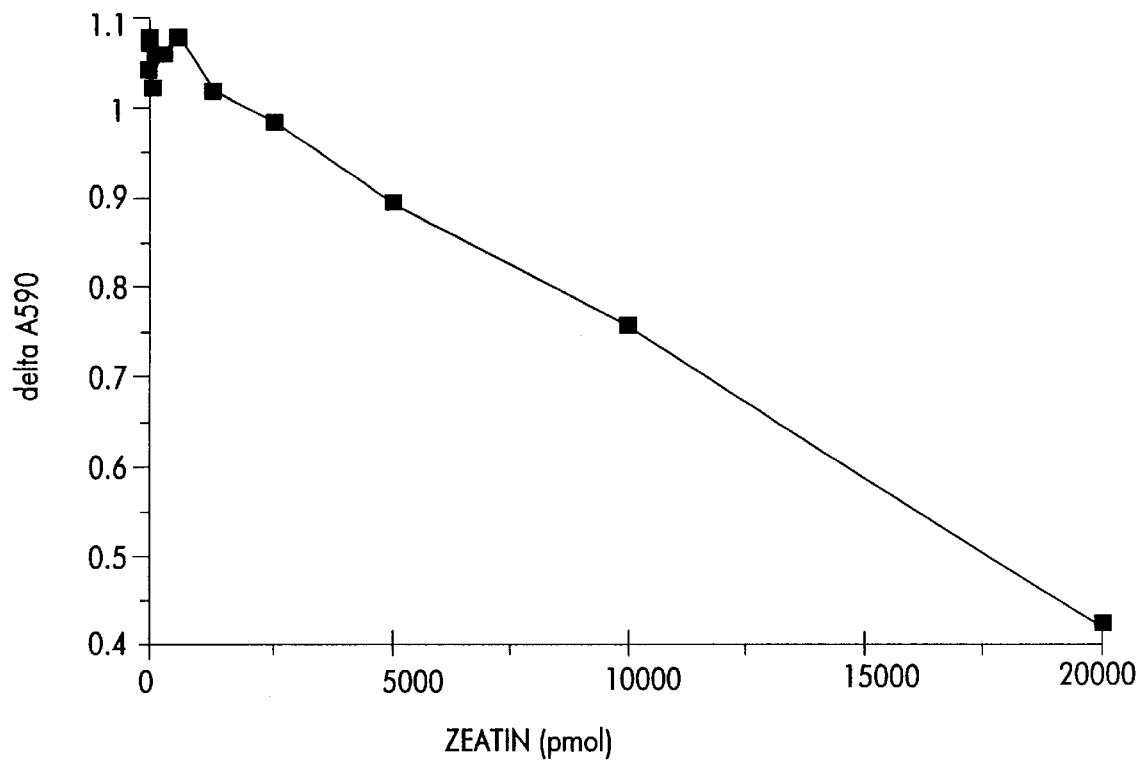
FIG. 3 shows the standard spectrophotometric absorbance curve (590 nm) obtained when using ckx1 to assay cytokinin concentrations in solution.

FIG. 3 illustrates the change in absorbance when the assay is used to measure the cytokinin zeatin. The method is capable of measuring as little as 2 nmol zeatin but, the major advantage of the assay over the prior art is its rapidity. Assays can be preformed in as little as five minutes, significantly faster than radioimmunoassays (MacDonald and Morris, 1985). Further, the method can be integrated in to cytokinin production systems by coupling the ckx1 gene to such cytokinin producing genes as ipt or tzs, in order to assay cytokinin production in vitro.

Example 4
Unregulated and Regulated Expression of ckx1 Constitutively and in the Roots of *Nicotiana tabacum*

The following procedure, which produces tobacco plants altered to express ckx1 constitutively and in their roots, is a slight modification of the standard protocols described in Draper, et al., 1988.

*Nicotiana tabacum* cultivar Xanthi is a standard tobacco line. Disarmed *Agrobacterium tumefaciens* strains such as LBA4404 (Hoekema, et al., 1985) are used. Murashige and Skoog salts, phytagar, sucrose, etc. are reagent or tissue-culture grade.

Figure 10:
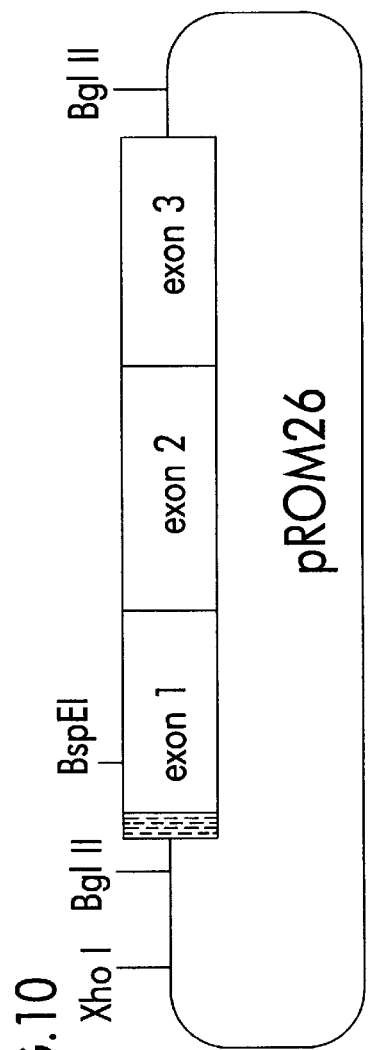
FIG. 10 is a diagram of DNA plasmid pROM26.

Three separate constructs were made with the ckx1 coding sequence (SEQ. ID NO. 3) to effect three different patterns of ckx1 expression in transformed tobacco plants. Constructs were based on the BIN19 plasmid primary vector (which includes an Agrobacterium compatible replication origin and kanamycin selection markers, Bevan, et al., 1984). The following constructs were made:

CaMV-ckx1-nos: The cauliflower mosaic virus promoter with a nos enhancer (U.S. Pat. No. 5,530,196), are present in pBI121 (FIG. 5)(available from Clonetech, Palo Alto, Calif.). The β-glucuronidase gene of pBI121 was excised with a BamHI/EcoIcrI digest. The coding sequence of ckx1 (SEQ. ID NO. 3) was obtained by a BglII digest of pROM26 (FIG. 10)(pROM24 (FIG. 9) altered by site-directed mutagenesis to contain another BglII and an XhoI restriction site). The final construct pROM30 (FIG. 13), which induces strong constitutive expression of ckx1, was created by digesting the altered pBI121 with BamHI and ligating in the ckx1 coding sequence.

Figure 4:
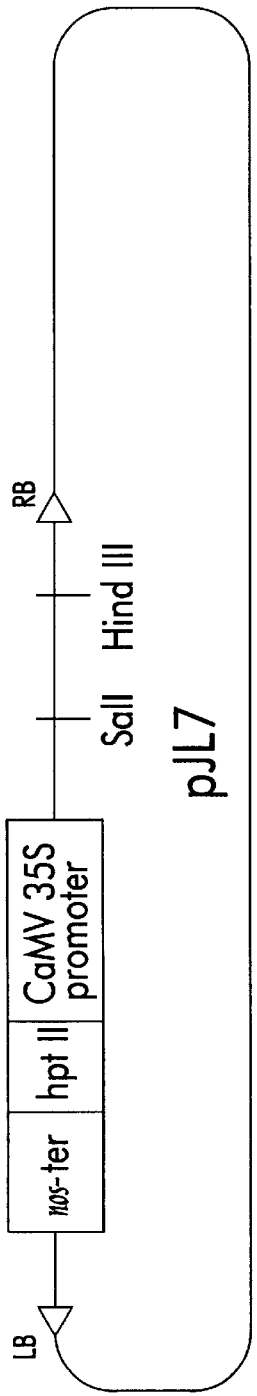
FIG. 4 is a diagram of DNA plasmid pJL7.
Figure 14:
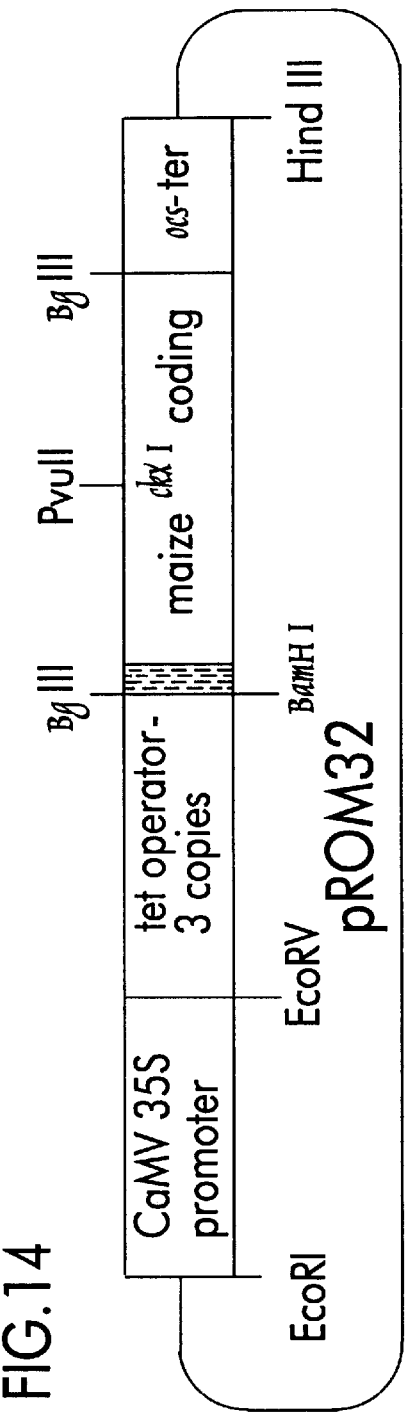
FIG. 14 is a diagram of DNA plasmid pROM32.

CaMV-tet-ckx1-ocs: The ckx1 coding region of pROM26 (FIG. 10) was isolated by BglII digestion and ligated into the BamHI site of pUCA7-TX (Gätz, et al., 1992) to form pROM32 (FIG. 14). The tetracycline-regulated operator element (U.S. Pat. No. 5,464,758) from pUCA7-TX and the inserted coding region were excised from pROM32 (FIG. 14) by PvuII digestion. The final construct pROM29 (FIG. 12), was produced by ligating the excerpt into the SalI site of pJL7 (FIG. 4)(a BIN19 type plasmid). When this construct is introduced into tobacco previously transformed to express the tet repressor protein, no ckx1 activity will be expressed until repression is relieved by addition of tetracycline. This construct may be of particular use in host organisms where strong constitutive expression of ckx1 results in abnormal growth patterns.

Figure 5:
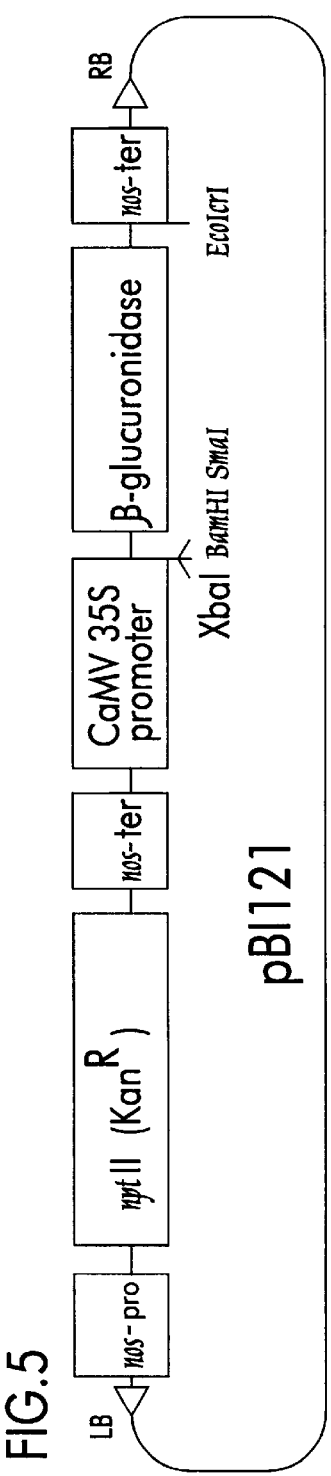
FIG. 5 is a diagram of DNA plasmid pBI121.
Figure 7:
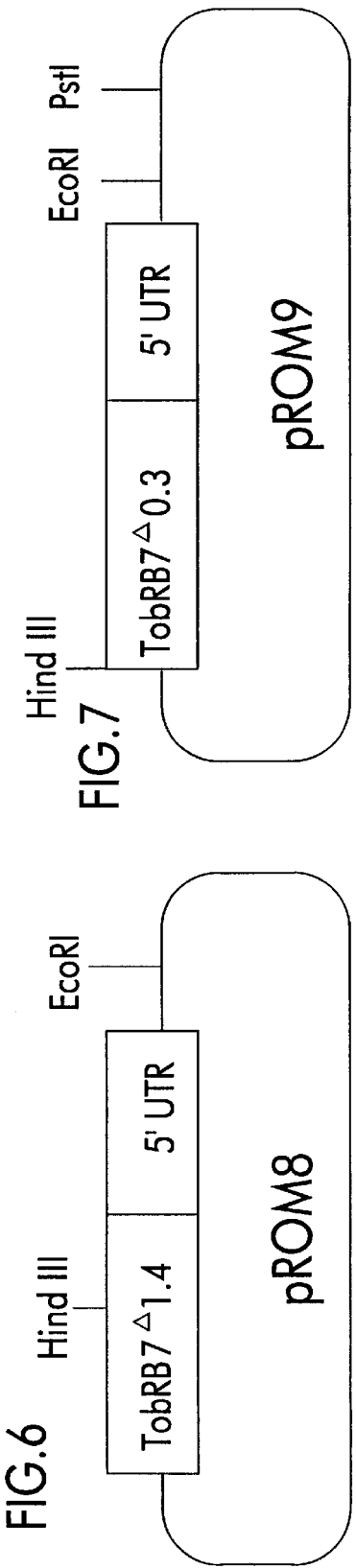
FIG. 7 is a diagram of DNA plasmid pROM9.
Figure 6:
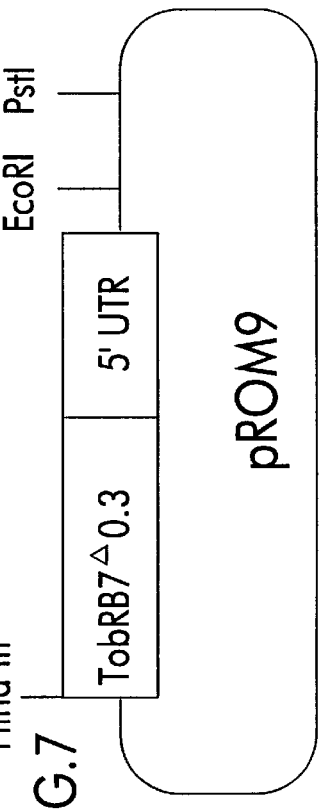
FIG. 6 is a diagram of DNA plasmid pROM8.
Figure 15:
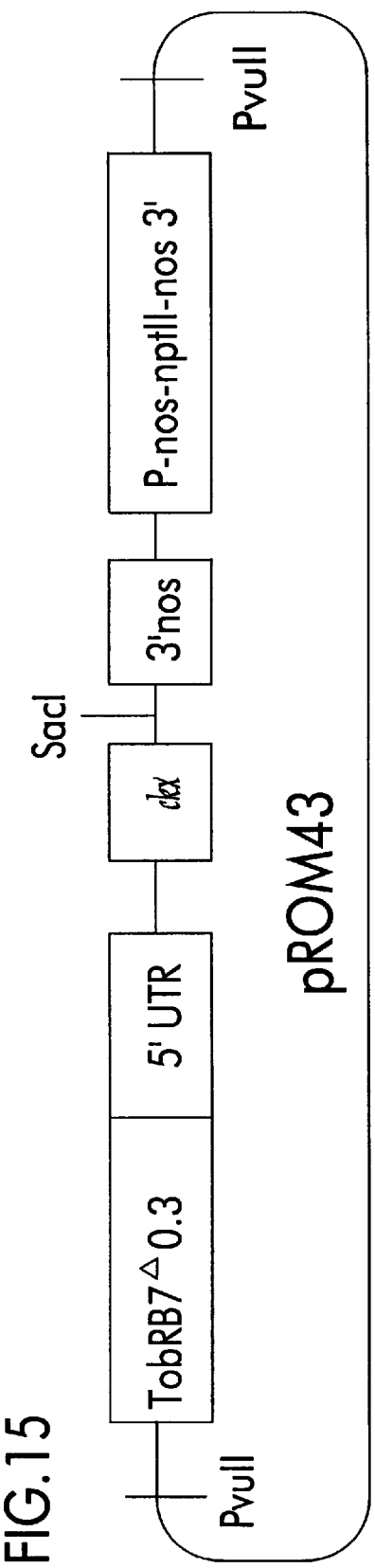
FIG. 15 is a diagram of DNA plasmid pROM43.

RB7-ckx1-nos: The tobacco RB7 root specific promotor (U.S. Pat. No. 5,750,386), was obtained by the following method. A fragment containing the promoter was PCR-amplified from tobacco genomic DNA using GACACCAT-TCCAAGCATACCCC (SEQ. ID NO. 19) and GTTCT-CACTAGAAAAATGCCCC (SEQ. ID NO. 20) as primers. This 1400 bp product was ligated into the pCRII plasmid (Invitrogen) to produce pROM8 (FIG. 6). The HindIII-EcoRI region of the insert, containing the nematode-specific portion of the promoter, was then excised and ligated into the HindIII-EcoRI site of pBluescriptII KS+ (Stratagene) to produce pROM9 (FIG. 7). The EcoRI-NsiI fragment of pROM24 (FIG. 9), containing the ckx1 coding sequence, was excised and ligated into the EcoRI-PstI site of pROM9, to make pROM28 (FIG. 11). The final construct pROM43 (FIG. 15), which induces expression of ckx1 in roots when the transformed plants' roots are attacked by nematodes, was produced by ligating a HindIII-SacI fragment of pROM28 into the HindIII-SacI site of pBI121 (FIG. 5).

| Media Component | MSS | PC | SI | MSSK |
| --- | --- | --- | --- | --- |
| MS Salts (g/l) | 4.3 | 4.3 | 4.3 | 4.3 |
| Sucrose (g/l) | 30.0 | 30.0 | 30.0 | 30.0 |
| Phytagar (g/l) | 7.5 | 5.0 | 5.0 | 7.5 |
| NAA (mg/l) | 0 | 1.0 | 1.0 | 0 |
| BAP (mg/l) | 0 | 0.1 | 0.1 | 0 |
| Timetin (mg/l) | 0 | 0 | 200 | 200 |
| Kanamycin (mg/l) | 0 | 0 | 50.0 | 50.0 |
| pH | 5.7 | 5.7 | 5.7 | 5.7 |

Nicotiana was continuously maintained by axenic shoot tip culture on MSS and sub-cultured at 4 week intervals.

The three binary plasmid constructs described above were electroporated into the disarmed A. tumefaciens host and transformants were grown under suitable selection (An, et al. 1985). Late-log phase cultures were used for transformation.

Young axenic tobacco leaves (3 to 4 weeks after tip culture) were dissected into 4 to 6 segments, excluding the largest vasculature. Segments were cultured on PC, abaxial side up, for 48 hours. The leaf pieces were then soaked in transformed A. tumefaciens culture diluted with water (1:1), for 1 hour. Pieces were then placed on the original PC medium for 48 hours. The leaves were then washed with water thoroughly and placed on SI medium and removed to fresh SI medium every 7 to 10 days. Although no adverse developmental effects were observed with Nicotiana transformants, the use of a non-substrate cytokinin such as benzylaminopurine, or tetracycline repression, may be needed for the culture of some host plants. Shoots were removed onto MSSK media when 1 cm long. Successive tip culture was carried out for 2 to 3 transfers, after which the transgenic plants were maintained on MSS media.

In light of the detailed description of the invention and the examples presented above, it can be appreciated that the several objects of the invention are achieved. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

BIBLIOGRAPHY

An, G., et al., 1985: "New cloning vehicles for transformation of higher plants," EMBO J. 4:277–84

Ault, G., 1994: "Type-specific amplification of viral DNA using touchdown and hot start PCR," J. Virol. Meth. 46:145–56.

Bechtold, N., et al., 1993: "In planta Agrobacterium mediated gene transfer by infiltration of adult Arabidopsis thaliana plants," CR Acad. Sci. Paris Sciences del la vie/life sciences 316:1194–99.

Bevan, M., 1984: "Binary Agrobacterium vectors for plant transformation," Nuc. Acids Rsrch. 12:8711–21.

Bird, A. F., et al., 1980: "The involvement of cytokinins in a host-parasite relationship between the tomato (Lycopersicon esculentum) and a nematode (Meloidogyne javanica)," Parasitology 80:497–505.

Bradford, M., 1976: "A Rapid and Sensitive Method for the Quantitation of Microgram Quantities of Protein Utilizing the Principle of Protein-Dye Binding," Analytical Biochem. 72:248–54.

Brownlee, B. G., et al., 1975: "3-Methyl-2-butenal: An Enzymatic Degradation Product of the Cytokinin, $N^6$-($\Delta^2$-isopentenyl)adenine," Can. J. Biochem. 53:37–41.

Burch, L. R., et al., 1992: "Cytokinin Oxidase and the Degradative Metabolism of Cytokinins," in Kaminek, et al. *Physiology and Biochemistry of Cytokinins in Plants*. pp. 229–32, STP Academic Publishing, The Hague, Netherlands.

Chen, H., et al., 1996: "Novel methods of generating specific oligonucleotide inhibitors of viral polymerases." *Methods in Enzymology* 275:503–20.

Davis, B., 1964: "Disk Electrophoresis II. Method and application to human serum proteins," *Ann. N.Y. Acad. Sci.* 121:404.

Dietrich, J. T., et al., 1995: "Changes in cytokinins and cytokinin oxidase activity in developing maize kernels and the effects of exogenous cytokinin on kernel development," *Plant Physiol. Biochem.* 33:327–36.

Draper, J., et al., 1988: *Plant Genetic Transformation and Expression: A Laboratory Manual*. Blackwell Scientific Publications.

Gätz, C., et al., 1992: "Stringent repression and homogenous de-repression by tetracycline of a modified CaMV 35 S promoter in intact tobaccod plants." *Plant J.* 2(3):397–404.

Hare, P. D., et al., 1994: "Cytokinin oxidase: Biochemical features and physiological significance," *Physiologia Plantarum* 91:128–35.

Hoekema, A., et al., 1985: "Non-oncogenic plant vectors for use in Agrobacterium binary systems," *Plant. Mol. Biol.* 5:85–89.

Horton, R. M., et al., 1989: "Engineering hybrid genes without the use of restriction enzymes: gene splicing by overlap extension," *Gene* 77:61–8.

Koziel, et al., 1993: "Field performance of elite transgenic maize plants expressing an insecticidal protein form *Bacillus thuringiensis*," *Bio/Technology* 11:194

Laemmli, U. K., 1970: "Cleavage of structural proteins during the assembly of the head of bacteriophage T4," *Nature* 227:680–685.

Liberos-Minotta, C., et al., 1995: "A calorimetric Assay for Cytokinin Oxidase," *Analytical Biochem.* 231:339–341.

MacDonald, E.M.S., et al., 1985: "Isolation of cytokinins by immunoaffinity chromatography and isolation by HPLC-radioimmunoassay," *Methods in Enzymology* 110: 347.

Maniatis, T., et al., 1990: *Molecular Cloning. A Laboratory Manual* 2nd Ed. Cold Spring Harbor Laboratory Press.

Møller, H. J., et al., 1995: "Improved method for Silver Staining of Glycoproteins in Thin Sodium Dodecyl Sulfate Polyacrylamide Gels," *Analytical Biochem.* 226:371–74.

Odell, et al., 1985: "Identification of DNA sequences required for activity of the cauliflower mosaic virus 35S promoter," *Nature* 313:810.

Ooms, G., et al., 1987: "Genetic transformation in two potato cultivars with T-DNA from disarmed Agrobacterium," *Theor. Appl. Genet.* 73:744–50.

Ornstein, L., 1964: "Disk Electrophoresis I. Background and theory," *Ann. N.Y. Acad. Sci.* 121:321.

Potrykus, 1991: "Gene transfer to plants: assessment of published approaches and results," *Annu. Rev. Plant Physiol., Plant Mol. Biol.,* 42:205.

Singer, B. S., et al., 1996: "Libraries for genomic SELEX," *Nucleic Acids Resrch.* 25:781–86.

Skory, C. D., et al., 1996: "Expression and secretion of the *Candida wickerhamii* extracellular beta-glucosidase gene, bgls, in *Saccharomyces cerevisiae*," *Current Genetics* 30:417–422.

Smith, C. T. S., et al., 1988: "Antisense RNA inhibition of polygalacturonase gene expression in transgenic tomatoes," *Nature* 334:724–26.

Su, W., st al., 1996: "Identification in vitro of a post-translational regulatory site in the hinge 1 region of Arabidopsis nitrate reductase," *Plant Cell* 8:519–27.

Van der Krol, A. R., et al., 1990: "Inhibition of flower pigmentation by antisense CHS genes: promoter and minimal sequence requirements for the antisense effect," *Plant Molec. Biol.* 14:457–66.

Williams, C. A, et al., 1967: *Methods in Immunology and Immunohistochemistry I* p. 319.

---

I claim as my invention:

1. An isolated nucleic acid polymer encoding a protein which exhibits cytokinin oxidizing activity, selected from the group consisting of:
   (a) SEQ. ID NO. 1,
   (b) a protein having an amino acid sequence which includes the amino acid sequence of SEQ. ID NO. 1, and
   (c) a protein including an amino acid sequence wherein at least 65% of the amino acids of the amino acid sequence correspond to the amino acid sequence of SEQ. ID NO. 1.

2. The isolated nucleic acid polymer of claim 1 which encodes SEQ. ID NO. 1.

3. An isolated nucleic acid polymer which encodes a protein which exhibits cytokinin oxidizing activity, wherein the nucleic acid polymer is selected from the group consisting of:
   (a) SEQ. ID NO. 2,
   (b) SEQ. ID NO. 3,
   (c) a nucleic acid polymer with a sequence described by SEQ. ID NO. 10,
   (d) a nucleic acid polymer whose sequence contains a sequence selected from the group consisting of SEQ. ID NO. 2, SEQ. ID NO. 3, or a nucleic acid polymer with a sequence described by SEQ. ID NO. 10,
   (e) a nucleic acid polymer which hybridizes to a nucleotide sequence selected from the group consisting of SEQ. ID NO. 2, SEQ. ID NO. 3, and a nucleic acid polymer with a sequence described by SEQ. ID NO. 10, under a wash stringency of 0.5× to 2× SSC buffer, 0.1% SDS, at 55–65° C., and
   (f) a nucleic acid polymer having a nucleotide sequence complementary to any of the nucleic acid sequences (a)–(e).

4. The isolated nucleic acid polymer of claim 3 wherein the polymer contains a sequence described by SEQ. ID NO. 10 or a sequence complementary to a sequence described by SEQ. ID NO. 10.

5. The isolated nucleic acid polymer of claim 3 wherein the polymer is SEQ. ID No. 2 or its complementary sequence.

6. The isolated nucleic acid polymer of claim 3 wherein the polymer is SEQ. ID No. 3 or its complementary sequence.

7. A host cell transformed with a vector containing a deoxyribonucleic acid polymer of claim 1.

8. The host cell of claim 7, wherein the host cell is a plant cell.

9. The host cell of claim 8, wherein the host plant cell is selected from the group consisting of:
   (a) *Nicotiana tabacum,*
   (b) *Arabidopsis thaliana,*
   (c) *Zea mays*
   (d) *Brassica spp* and
   (e) *Oryza sativa.*

10. The host cell of claim 7 wherein the host cell is selected from the group consisting of:
    (a) *Pichia pastoris* and
    (b) *Escherichia coli.*

11. A plant regenerated from the host plant cell in claim 8.

12. A method for producing a protein exhibiting cytokinin oxidizing activity in a host cell, comprising
    (a) constructing a vector containing a nucleic acid polymer of claim 1 and an expression regulatory sequence operational in the host cell;
    (b) transfecting a host cell suitable for protein production with the vector; and
    (c) expressing the protein in the host cell.

13. The method of claim 12 wherein the vector is a plasmid comprised of DNA.

14. The method of claim 12, wherein the host cell is selected from the group consisting of:
    (a) *Pichia pastoris* and
    (b) *Escherichia coli.*

15. The method of claim 12, wherein the host cell secretes said protein into a culture medium, and wherein the method further comprises purifying said protein from the culture medium.

16. The method of claim 12, wherein the host cell is a plant cell.

17. The method of claim 16, wherein the host plant cell is selected from the group consisting of:
    (a) *Nicotiana tabacum,*
    (b) *Arabidopsis thaliana,*
    (c) *Zea mays*
    (d) *Brassica spp* and
    (e) *Oryza sativa.*

18. A method of moderating cytokinin-associated pathogenesis in a plant comprising transforming a plant cell with a nucleic acid polymer construct which contains:
    (a) a nucleic acid polymer of claim 1, and (b) an expression regulatory sequence operational in the host plant; and regenerating a plant from the transformed plant cell.

19. A method as set forth in claim 18 wherein the expression regulatory sequence is selected from the group consisting of constitutive promoters, inducible promoters, repressors, and enhancers.

20. An isolated nucleic acid polymer which encodes a protein which exhibits cytokinin oxidizing activity, wherein the nucleic acid polymer is selected from the group consisting of:

(a) a nucleic acid polymer which encodes a protein comprising an amino acid sequence of at least 20 amino acids, wherein 90% of the amino acids in said amino acid sequence are the same as the corresponding amino acids of a portion of SEQ. ID NO. 1 of the same size, and (b) a nucleic acid polymer having a nucleotide sequence complementary to a nucleic acid sequence of (a).

* * * * *